United States Patent
Marsh et al.

(10) Patent No.: US 10,837,967 B2
(45) Date of Patent: *Nov. 17, 2020

(54) 1,1'-[[(SUBSTITUTED ALKYL)IMINO]BIS(ALKYLENE)]BIS-FERROCENES AND THEIR USE IN I ELECTROCHEMICAL ASSAYS BY LABELLING SUBSTRATES OF INTEREST

(71) Applicant: Atlas Genetics Limited, Trowbridge (GB)

(72) Inventors: Barrie Marsh, Trowbridge (GB); Christopher Frost, Bath and Northeast (GB); David Pearce, Trowbridge (GB)

(73) Assignee: Binx Health Limited, Trowbridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/664,306

(22) Filed: Oct. 25, 2019

(65) Prior Publication Data

US 2020/0057071 A1 Feb. 20, 2020

Related U.S. Application Data

(63) Continuation of application No. 15/906,241, filed on Feb. 27, 2018, now Pat. No. 10,502,744, which is a continuation of application No. 14/410,296, filed as application No. PCT/GB2013/051643 on Jun. 21, 2013, now abandoned.

(30) Foreign Application Priority Data

Jun. 22, 2012 (GB) .................. 1211157.1

(51) Int. Cl.
G01N 33/58 (2006.01)
C12Q 1/6816 (2018.01)
C07F 17/02 (2006.01)

(52) U.S. Cl.
CPC ............. *G01N 33/58* (2013.01); *C07F 17/02* (2013.01); *C12Q 1/6816* (2013.01)

(58) Field of Classification Search
CPC . C12Q 1/6816; C12Q 2563/113; C07F 17/02; G01N 33/58
See application file for complete search history.

(56) References Cited

U.S. PATENT DOCUMENTS

| | | | |
|---|---|---|---|
| 5,925,778 A | 7/1999 | Pugin | |
| 7,803,572 B2 | 9/2010 | Braven et al. | |
| 9,127,308 B2 | 9/2015 | Braven et al. | |
| 10,502,744 B2* | 12/2019 | Marsh | G01N 33/58 |
| 2005/0221315 A1* | 10/2005 | Braven | C12Q 1/6823 |
| | | | 435/6.18 |
| 2014/0051080 A1 | 2/2014 | Sharp et al. | |
| 2015/0159203 A1 | 6/2015 | Braven et al. | |
| 2016/0025703 A1 | 1/2016 | Braven et al. | |
| 2018/0252664 A1 | 9/2018 | Marsh et al. | |
| 2018/0299454 A1 | 10/2018 | Marsh et al. | |

FOREIGN PATENT DOCUMENTS

| | | |
|---|---|---|
| WO | 2003074731 A2 | 9/2003 |
| WO | 2005005657 A1 | 1/2005 |
| WO | 2011/073675 A2 | 6/2011 |
| WO | 2012/085591 A1 | 6/2012 |

OTHER PUBLICATIONS

Alvarez, 1999, Structural and pH Control on the Elctronic Communication between Two Identical Forrocene Sites, Organometallics, 18:5733-5734.
Baldoli, 2006, A new triferrocenyl-tris(hydroxymethyl)aminomethane derivative as a highly sensitive electrochemical marker of biomolecules: Application to the labeling of PNA monomers and their electrochemical characterization, Chem Eru J, 12(5):4091-4100.
Brown, 1933, Electrochemistry of chlorinated ferrocenes: stability of chlorinated ferrocenium ions, J Chem Soc, Dalton Trans, pp. 835-840.
Cho, 1999, Chiral C2-symmetrical bisferrocenyldiamines as ligands for transition metal catalyzed asymmetric cyclopropanation and aziridination, Tetrahedron: Asymmetry, 10:3833-3848.
Database CA [Online], Chemical Abstracts Service, Columbus, Ohio, US; Hu, Xiang Ping, et al: Synthesis and Potential Application of Novel C2-Symmetrical bis(ferrocenyl) P2N ligand, 2004.
Dietrich, 2011, Amidoamine-based dendrimers with end-grafted Pd—Fe unites: Synthesis, characterization and their use in the Heck reaction, Journal of Organometallic Chemistry, 696:739-747.
Dong-Jei Cho, 1999, Chiral C2-Symmetric Bisferrocenyldiamines as Ligands for Transition Metal Catalyzed Asymmetric Cyclopropanation and Aziridination, Tetrahedron: Asymmetry, 10(19):3833-3848.
European Search Report issued in European Application No. 13731474. 6, dated Apr. 24, 2020, 11 pages.
Hu, 2003, Synthesis and Potential Application of Novel C2-Symmetrical Bis(ferrocenyl) P2N Ligand, Chinese Chemical Letters, 14:1113-1115.

(Continued)

Primary Examiner — Galina M. Yakovleva
(74) Attorney, Agent, or Firm — Brown Rudnick LLP; Thomas C. Meyers

(57) ABSTRACT

Compounds of general formula I wherein Fc and Fc' may be the same or different and are substituted ferrocenyl moieties having at least one ring substituent selected from sulfur-containing groups, phosphorus-containing groups, iodo, chloro, silyl, fluoroalkyl groups containing two or more fluorine atoms, heteroaryl, substituted phenyl, and cyano, wherein if present as sole substituent the cyano group is located on the proximal cyclopentadienyl ring; X is a spacer, Y is a spacer, Z is a spacer; and R is a linker group. Compound I may be used to make labelled substrates, functionalised compounds for making labelled substrates and may be used as labels in an electrochemical assay.

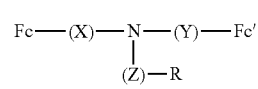

2 Claims, No Drawings

(56) References Cited

OTHER PUBLICATIONS

International Search Report for PCT/GB2013/051643, dated Oct. 29, 2013, 5 pages.
Kerr, 2000, Synthesis and Structure of N-ferrocenyl glycosylamines; redox chemistry of O-ferrocenylglycosides and N-ferrocenyl glycosylamines, J Chem Soc, Dalton Trans, pp. 1411-1417.
Kuhnert, 2008, Phosphinoferrocenyl-terminated amidoamines: Synthesis and catalytic utilization in palladium-mediated C—C bond forming reactions, J. Molecular Catalysis A: Chemical 285, pp. 41-47.
Lamarc, 2010, Preparation of planar-chiral multidonor phosphanylferrocene carboxamides and their application as ligands for palladium-catalyzed asymmetric allylic alkylation, Applied Organometallic Chemistry, 24:326-331.
Raghunath, 2005, Ferrocenyl bis-phosphine ligands bearing sulfinyl, sulfonyl or sulfenyl groups: applications in asymmetric hydrogenation and allytic alkylation reactions, Tetrahedrom: Asymmetry, 16:3676-3681.
Romanov, 2009, Monohalogenated ferrocenes $C_5H_5FeC_5H_4$ X (X=Cl, Br and I) and a second polymorph of $C_5H_5FeC_5H_4I$, Acta Crystallogr, C65, m426-m430.

\* cited by examiner

1,1'-[[(SUBSTITUTED ALKYL)IMINO]BIS(ALKYLENE)]BIS-FERROCENES AND THEIR USE IN I ELECTROCHEMICAL ASSAYS BY LABELLING SUBSTRATES OF INTEREST

CROSS-REFERENCE TO RELATED APPLICATIONS

This application is a continuation of U.S. patent application Ser. No. 15/906,241, filed on Feb. 27, 2018, which is a continuation of U.S. patent application Ser. No. 14/410,296 entitled "1,1 [[(SUBSTITUTED ALKYL)IMINO]BIS (ALKYLENE)]BIS-FERROCENES AND THEIR USE IN I ELECTROCHEMICAL ASSAYS BY LABELLING SUBSTRATES OF INTEREST," filed on Dec. 22, 2014, which is a national stage application, filed under 35 U.S.C. § 371, of International Application No. PCT/GB2013/051643, filed on Jun. 21, 2013, and claims the benefit of, and priority to, GB Patent Application No. 1211157.1, filed on Jun. 22, 2012, the complete contents of which are hereby incorporated herein by reference in their entirety for all purposes.

FIELD OF THE INVENTION

The invention relates to electrochemical detection methods. More especially, the invention relates to electrochemical assays, to electrochemically active labels for use in electrochemical detection methods, and to their use.

BACKGROUND OF THE INVENTION

The detection of certain biological molecules plays an important part in many aspects of life. For example, in the medical field, there is an ever-present need to detect bacterial or viral pathogens, or biological molecules. Other fields in which sensitive assays are essential include the food and beverage industries.

WO03/074731 discloses a method of probing for a nucleic acid. A nucleic acid solution is contacted with an oligonucleotide probe with an electrochemically active marker. The probe is caused to at least partially hybridise with any complementary target sequence which may be present in the nucleic acid solution. Following enzymatic degradation of the nucleic acid probe, information is electrochemically determined relating to the marker. Compounds for use in the method are also disclosed.

WO2005/005657 discloses a method of detecting protease activity in which a sample solution is contacted with a protease substrate with an electrochemically active marker, providing conditions under which any protease which may be present in the sample may degrade the protease substrate and information relating to the electrochemically active marker is electrochemically determined. Certain novel compounds for use in the process were also disclosed.

WO2012/085591 describes certain diferrocenyl compounds for use as electrochemical labels.

There is a continuing need to develop labels that enable detection of the presence in small concentrations of biological substrates or indicators, for example, nucleic acids (in isolated form or in the form of larger molecules, for example, natural or synthetic oligonucleotides), or amino acids (in isolated form or in the form of larger molecules, for example, natural or synthetic peptides). In particular, there is a continuing need for new labels with different oxidation potentials and/or with different chemical or physical properties thereby widening the range of possible assays available and increasing the scope for the development of multiplex reactions.

SUMMARY OF THE INVENTION

The invention provides a compound according to general formula I

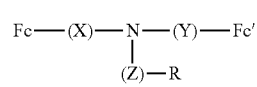

in which:
Fc is a substituted ferrocenyl moiety having at least one ring substituent selected from sulfur-containing groups, phosphorus-containing groups, iodo, chloro, silyl, fluoroalkyl groups containing two or more fluorine atoms, heteroaryl, substituted phenyl, and cyano, wherein if present as sole substituent the cyano group is located on the proximal cyclopentadienyl ring;
Fc' is a substituted ferrocenyl moiety having at least one ring substituent selected from sulfur-containing groups, phosphorus-containing groups, iodo, chloro, silyl, fluoroalkyl groups containing two or more fluorine atoms, heteroaryl, substituted phenyl, and cyano, wherein if present as sole substituent the cyano group is located on the proximal cyclopentadienyl ring, and may be the same as or different from Fc;
X is a spacer
Y is a spacer
Z is a spacer; and
R is a linker group.

The invention also provides use as a label in an electrochemical assay of a compound of general formula I:

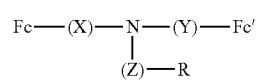

in which:
Fc is a substituted ferrocenyl moiety, having at least one ring substituent selected from sulphur-containing groups, phosphorus-containing groups, iodo, chloro, silyl, fluoroalkyl groups containing two or more fluorine atoms, heteroaryl, substituted phenyl, and cyano, wherein if present as sole substituent the cyano group is located on the proximal cyclopentadienyl ring;
Fc' is a substituted ferrocenyl moiety having at least one ring substituent selected from sulphur-containing groups, phosphorus-containing groups, iodo, chloro, silyl, fluoroalkyl groups containing two or more fluorine atoms, heteroaryl, substituted phenyl, and cyano, wherein if present as sole substituent the cyano group is located on the proximal cyclopentadienyl ring, and may be the same as or different from Fc;
X is a spacer
Y is a spacer
Z is a spacer; and
R is a linker group.

The compounds used in accordance with the invention have been found to be effective labels for use in electrochemical assays. In particular, the compounds may be used to form labelled substrates. Molecules of interest as substrates that may be labelled include, but are not limited to: amino acids, nucleotides, nucleosides, sugars, peptides, proteins, oligonucleotides, polynucleotides, carbohydrates and derivatives or synthetic analogs of any of those molecules. Other substrates that might be labelled using the compounds of the invention include latex/paramagnetic microparticles and nanoparticles. The labelling compounds of general formula I and labelled molecules including labels derivable from the labelling compounds are potentially useful in electrochemical techniques in which their electrochemical characteristics can be utilized to derive information about the labels or their environment. For example, the compounds of the invention may find use in a method as described in WO03/074731 or in a method as described in WO2005/005657. The labelling compounds of the invention and the labelled substrates derived therefrom offer characteristics which make them useful complements to previously known labelling compounds, permitting a wider spectrum of applications, for example, offering additional opportunities for avoidance of conditions under which measurement potential may be compromised by interference with impurities that may be present and/or offering differing electrochemical potential values and/or allowing more greater flexibility in multiplex assays. A number of the compounds and the corresponding labelled substrates have relatively high electro potential values, as illustrated in particular by Example 4 below. It is believed that, especially, compounds of the invention having sulfur-containing or phosphorus-containing substituents and their corresponding labelled substrates will be useful in providing for assays in which the measurement potential will be relatively high, for example, in excess of 400 mV, for example in excess of 450 mV or even in excess of 500 mV. Compounds having electrochemical potentials of at least 450 mV, for example 500 mV or more, will be particularly useful in extending the range of available potential values and therefore, for example, in potentially providing for more effective multiplex assays. Other compounds of the invention having highly electron-withdrawing substituents, for example, trifluoromethyl or cyano, are believed to have similar advantages in terms of offering high electrochemical potential values thereby extending the range of useful labels and labelled substrates. Additionally, some compounds of the invention and the corresponding labelled substrates offer the advantage of having a narrower voltage peak, which is advantageous in providing for the option of utilising a greater number of labels in a multiplex assay, since the narrower measurement peaks result in wider gaps between peaks, which may be utilised if desired by incorporating additional labels with potentials that will be within the gaps.

In all aspects of the invention, the following spacers are preferred: X is a C1 to C6 alkylene chain which is optionally interrupted by —O—, —S—, or —NR$^5$—, in which R$^5$ represents hydrogen or C1 to C6 alkyl; Y is a C1 to C6 alkylene chain which is optionally interrupted by —O—, —S—, or —NR$^5$—, in which R$^5$ represents hydrogen or C1 to C6 alkyl; and Z is a C1 to C12 alkylene chain which may optionally be substituted and/or may optionally be interrupted by —O—, —S—, cycloalkyl, —CO—, —CONR$^1$—, —NR$^1$CO— or —NR$^1$— in which R$^1$ represents hydrogen or C1 to C4 alkyl.

In the compounds used according to the invention it is preferred that X represents C1- to C6-alkylene optionally interrupted by oxygen; Y represents C1 to C6-alkylene optionally interrupted by oxygen; and Z represents C1 to C8 alkylene optionally interrupted by oxygen. Thus in these embodiments X, Y and Z can be represented by the formula $(CH_2)_a$—O—$(CH_2)_b$, wherein a≥0 and b≥0. For X and Y, a+b=1-6. For Z, a+b=1-8. Ideally a≥1 and b≥1.

X is preferably —$(CH_2)_x$— in which x is from 1 to 6, preferably 1 to 4, especially 1 or 2; or C1 to C6-alkylene interrupted by oxygen, for example —$(CH_2)_3$—O—$CH_2$—, —$(CH_2)_2$—O—$(CH_2)_2$—, or —$CH_2$—O—$(CH_2)_3$—.

Y is preferably —$(CH_2)_y$— in which y is from 1 to 6, preferably 1 to 4, especially 1 or 2; or C1 to C6-alkylene interrupted by oxygen, for example —$(CH_2)_3$—O—$CH_2$—, —$(CH_2)_2$—O—$(CH_2)_2$— or —$CH_2$—O—$(CH_2)_3$—.

Preferably X and Y are the same. Preferably Fc and Fc' are the same and X and Y are the same.

In an embodiment. Z is a C1 to C12 alkylene chain which may optionally be substituted and/or may optionally be interrupted by —O—, —S— or —NR$^1$— in which R$^1$ represents hydrogen or C1 to C4 alkyl. Preferably Z is —$(CH_2)_z$— in which z is from 1 to 8, with z preferably representing from 1 to 6, especially from 2 to 6; or is C1 to C8 alkylene interrupted by oxygen, for example —$(CH_2)_2$—O—$(CH_2)_3$— or —$(CH_2)_3$—O—$(CH_2)_2$—. In one preferred embodiment: X is —$(CH_2)_x$— in which x is 1 or 2; Y is —$(CH_2)_y$— in which y is 1 or 2; and Z is —$(CH_2)_y$— in which z is from 1 to 8. Where X and Y represent an alkylene chain interrupted by —NR$^5$—, R$^5$ preferably represents hydrogen or C1 to C4 alkyl, more preferably hydrogen.

In one preferred embodiment, the invention provides use, as an electrochemical label, of a compound of the general formula II:

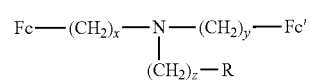

II in which:
  Fc is a substituted ferrocenyl moiety as defined above with reference to general formula I.
  Fc' is a substituted ferrocenyl moiety as defined above with reference to general formula I, and may be the same as or different from Fc;
  x is 1 or 2;
  y is 1 or 2;
  z is from 1 to 8;
  and R is a linker group.
  Preferably, x and y are each equal to 1.
  It is preferred that the ferrocenyl moieties are the same, and it is therefore preferred that Fc and Fc' carry the same substituents in the same positions.

Except where the contrary is apparent from the context, the term "substrate" is used throughout the remainder of this document to include both naturally occurring substrates and synthetic substrates, and references herein to amino acids, nucleotides, nucleosides, sugars, peptides, proteins, oligonucleotides, polynucleotides, or carbohydrates, are to be understood as referring to naturally occurring or synthetic amino acids, nucleotides, nucleosides, sugars, peptides, proteins, oligonucleotides, polynucleotides, or carbohydrates. Substrates can also be polypeptides. Synthetic substrates include synthetic analogues of naturally occurring substrates. Substrates include single nucleotides and single amino acids. In the case of an assay relying upon cleavage of a substrate, for example by an enzyme, a single amino acid may be regarded as a substrate because, although it lacks an internal bond capable of being cleaved by a protease enzyme, such a bond may be formed through the attachment of a marker. Where derivatives of naturally occurring substrates are referred to herein, those derivatives may be naturally occurring derivatives or synthetic derivatives of the substrate.

The invention provides a method of detecting a chemical entity using a compound according to the invention. Use in an electrochemical assay according to the invention may be for example in an assay for detecting an electrochemically labelled substrate. The electrochemical assay may for example be an assay for determination of the amount of an electrochemically labelled substrate. The assay may advantageously be for detecting or determining the amount of a labelled substrate wherein the labelled substrate is selected from amino acids, nucleotides, nucleosides, sugars, peptides, proteins, oligonucleotides, polynucleotides, carbohydrates, microparticles and nanoparticles. In certain preferred embodiments, the assay is for detecting or determining the amount of a labelled substrate in which the labelled substrate is selected from nucleotides, nucleosides, oligonucleotides, and polynucleotides. In another advantageous embodiment, the assay is for detecting or determining the amount of a labelled substrate in which the labelled substrate is selected from amino acids, peptides, and proteins.

For the purpose of attachment to substrates, the label may be functionalised by addition of a functionalising group. Thus, the invention further provides functionalised derivatives comprising a moiety derivable from the compounds of the invention attached to a functionalising group suitable for enhancing attachment to a substrate.

The invention also provides a method for manufacturing a functionalized labelling compound comprising a label moiety for use in an electrochemical assay, comprising reacting a compound of general formula I:

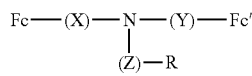

I in which:
Fc is a substituted ferrocenyl moiety having at least one ring substituent selected from sulphur-containing groups, phosphorus-containing groups, iodo, chloro, silyl, fluoroalkyl groups containing two or more fluorine atoms, heteroaryl, substituted phenyl, and cyano, wherein if present as sole substituent the cyano group is located on the proximal cyclopentadienyl ring,
Fc' is a substituted ferrocenyl moiety having at least one ring substituent selected from sulphur-containing groups, phosphorus-containing groups, iodo, chloro, silyl, fluoroalkyl groups containing two or more fluorine atoms, heteroaryl, substituted phenyl, and cyano, wherein if present as sole substituent the cyano group is located on the proximal cyclopentadienyl ring, and may be the same as or different from Fc;
X is a spacer
Y is a spacer
Z is a spacer; and
R is a linker group,
with a functionalising compound to obtain a funtionalised labelling compound of general formula III:

A-L-F    III in which A represents

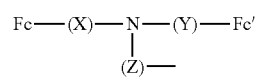

Ia wherein
Fc, Fc', X, Y and Z are as defined above with reference to general formula I;
F represents a functionalising moiety, especially a functionalising moiety for reacting with a substrate for attachment of the labelling moiety to the substrate; and
L represents a linker moiety.

The linker moiety L will generally be a linker moiety derivable from the linker group R. For example where R is or contains an OH group L will usually represent or comprise —O—.

Furthermore the invention provides a method for the manufacture of a labelled substrate, comprising reacting a compound of general formula III:

A-L-F    III in which A, L and F are as defined above;
with a substrate to form a labelled substrate.

The invention moreover provides a functionalised labelling compound for use in the manufacture of a labelled substrate, the functionalised labelling compound having the general formula III:

A-L-F    III in which A, L and F are as defined above.

The invention also provides a labelled substrate for use in an electrochemical assay, the labelled substrate being of general formula IIIa:

A-L-F'—[S]    IIIa in which A represents

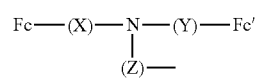

Ia in which:
Fc is a substituted ferrocenyl moiety having at least one ring substituent selected from sulphur-containing groups, phosphorus-containing groups, iodo, chloro, silyl, fluoroalkyl groups containing two or more fluorine atoms, heteroaryl, substituted phenyl, and cyano, wherein if present as sole substituent the cyano group is located on the proximal cyclopentadienyl ring,
Fc' is a substituted ferrocenyl moiety having at least one ring substituent selected from sulphur-containing groups, phosphorus-containing groups, iodo, chloro, silyl, fluoroalkyl groups containing two or more fluorine atoms, heteroaryl, substituted phenyl, and cyano, wherein if present as sole substituent the cyano group is located on the proximal cyclopentadienyl ring, and may be the same as or different from Fc;
X is a spacer
Y is a spacer
Z is a spacer;
L-F' represents a linking moiety; and
[S] represents a substrate.

The linking moiety -L-F'— is in general a moiety derivable from the moiety -L-F according to general formula III or a moiety derivable from the moiety —R according to general formula I. In an embodiment the linking moiety -L-F'— is a moiety derivable from the moiety -L-F according to general formula III.

By analogy, the invention also provides a labelled substrate for use in an electrochemical assay, the labelled substrate being of general formula IIIb:

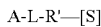  IIIb where R' is a residue of R formed when reacting a compound of the invention with a substrate.

The invention further provides assays comprising substrates according to the invention.

DETAILED DESCRIPTION

Except where it is clear that the contrary is intended, references herein to "alkyl" are to straight- or branched-chain alkyl groups preferably having from 1 to 6 carbon atoms, more preferably from 1 to 4 carbon atoms, optionally interrupted by a heteroatom selected from O, S and N and/or optionally having one or more substituents; or to cycloalkyl groups. Illustrative alkyl groups include, for example, methyl, ethyl, n-propyl, i-propyl, n-butyl, t-butyl.

References herein to "cycloalkyl" are to cycloalkyl groups having up to eight, preferably up to six, ring atoms, optionally including one or more heteroatoms. Illustrative cycloalkyl groups include, for example, cyclohexyl and heterocyclic groups such as piperidinyl and morpholinyl.

References herein to "alkenyl" are to straight- or branched-chain alkenyl groups preferably having from 1 to 6 carbon atoms, more preferably from 1 to 4 carbon atoms, optionally having one or more substituents. Illustrative alkenyl groups include, for example, ethenyl, propenyl, butenyl.

The term "haloalkyl" is used herein, except where the contrary is indicated, to refer to alkyl groups having one or more halogen atoms present as substituents, said one or more halogen atoms being selected from fluorine, chlorine, bromine and iodine.

Unless the contrary is indicated, "sulfur-containing group" will be understood as including, without limitation, substituent groups including an —S(O)$_2$— moiety (referred to herein as "sulfonyl"), an —S(O)— moiety (referred to herein as "sulfinyl") or an —S— moiety (referred to herein as "sulfenyl"). Preferred sulfur-containing groups that may be present as substituents on the ferrocenyl rings in accordance with the invention are those in which the sulfur atom is directly bonded to a ring carbon.

Unless the contrary is indicated, "phosphorus-containing group" will be understood as including, without limitation, substituent groups including those based on phosphines or phosphine oxides, more particularly phosphanyl (>P—) and phosphinyl (>P(O)—) groups. Preferred phosphorus-containing groups that may be present as substituents on the ferrocenyl rings in accordance with the invention are those in which the phosphorus atom is directly bonded to a ring carbon.

References herein to "heteroaryl" are to be understood as including any single or fused aromatic moiety including one or more heteroatoms, the heteroatoms preferably being selected from oxygen, sulphur and nitrogen. Where more than one heteroatom is present the heteroatoms may be the same or different, each advantageously being independently selected from oxygen, sulphur and nitrogen. Illustrative heteroaryl groups include without limitation furanyl, imidazolyl, thiazolyl.

References herein to "aryl" are to be understood as including any single or fused aromatic ring system and include both hetero and other ring systems.

The expression "substituted phenyl" as used herein includes any phenyl group having one or more substituents attached to the phenyl ring, at any ring carbon atom of the ring. Where there is mom than one substituent on the phenyl ring those substituents may be the same or may be different from one another.

The application of electrochemical detection has a number of advantages over fluorescent detection. Electrochemical detection has the potential for very high levels of sensitivity and exhibits a wider linear dynamic range than fluorescence. There is no requirement for samples to be optically clear. There is also less interference from background contaminants (many biological samples auto-fluoresce).

Electrochemical detection is based on the observation that an electrochemically active marker exhibits different electrochemical characteristics depending on whether or not it is attached to a substrate and on the nature of the substrate. For example, in the case of an electrochemical label attached to an amino acid, the exhibited characteristics will depend not only on the identity of the amino acid but also on whether or not that amino acid residue is incorporated into a peptide or protein, and on the length of any such peptide or protein. Under appropriate circumstances, the electrochemical activity of a marker attached to an amino acid residue can change by a detectable degree following loss of attachment of a single or very few amino acid residues.

The size and characteristics of a molecule to which an electrochemically active marker is attached influence the observable characteristics of the electrochemical marker. That may occur, for example, by influencing the rate of migration of the marker by diffusion or its rate of migration in response to an electric field.

Electrochemical activity of a marker may also be influenced by steric effects resulting from the presence of the molecule to which it is linked. For example, steric hindrance may prevent the marker from approaching an electrode and accepting or donating electrons.

If the marker is attached to a peptide then the secondary structure of the peptide (as largely determined by the primary sequence) may influence the physical properties of the marker. For example, if the marker is attached to an amino acid residue in a peptide such that the structure of the peptide sterically hinders the electrochemically active marker then the signals observable by voltammetry may be reduced. Digestion of the peptide may destroy or release secondary structure elements and thus reduce or abolish the influence of the peptide structure on the marker. Accordingly, digestion of the peptide results in a change, usually an increase, in the electrochemical signal produced by the marker moiety. In a differential pulse voltammetry experiment, the Faradaic current response at a particular applied voltage may increase upon digestion of the peptide.

Analogously, if a marker is attached to a nucleotide, the electrochemical characteristics will be influenced by whether or not the nucleotide is incorporated into an oligonucleotide, upon the length of that oligonucleotide, and upon the sequence of the oligonucleotide especially in the vicinity of the point of attachment.

The information relating to the electrochemically active marker can be obtained by voltammetry or by an amperometric method. Differential pulse voltammetry is particularly suitable. If desired, the electrochemical detection step may be carried out using one or more electrodes covered by a membrane which is able selectively to exclude molecules based on one or more characteristics, for example, size, charge or hydrophobicity. That may assist in eliminating background noise current arising from, for example, charged species in the solution.

In the compounds (including labelling compounds, functionalised labelling compounds and labelled substrates) used in accordance with the invention, including the compounds according to general formulae I, II and III, the labelled substrate of general formula IIIa and the label moiety of general formula Ia, the two ferrocenyl groups Fc and Fc' are each independently selected from substituted ferrocenyl groups having one or more substituents as defined above with reference to general formula I. One or both pentadienyl rings of one or each of the ferrocenyl moieties may be substituted by one or more substituents, the nature and location of which are selected so as to influence in a desired manner the redox characteristics of the ferrocene moiety. In addition to the substituents defined above, the pentadienyl rings of the ferrocenyl moiety may further be substituted by any further ring substituent(s) that do not materially reduce the electrochemical sensitivity of the label, or by any further ring substituent(s) that will enhance the electrochemical or other characteristics of the label in any respect.

In a preferred embodiment. Fc and Fc' are the same and each comprise at least one substituent selected from the group consisting of:
sulfur-containing groups selected from sulfenyl, sulfinyl and sulfonyl groups, phosphorus-containing groups selected from phosphanyl and phosphinyl groups, iodo, chloro,
fluoroalkyl groups containing two or more fluorine atoms, especially trifluoroalkyl, heteroaryl, and
substituted phenyl.

In another embodiment, Fc and Fc' are the same and there is as substituent a cyano group located on the respective proximal cyclopentadienyl ring of each of said Fc and Fc' moieties.

In one preferred embodiment of the invention. Fc and Fc' are the same and each comprise at least one ring substituent selected from sulfur-containing groups and phosphorus-containing groups. In one illustrative Example below from the group consisting of sulfur-containing groups and phosphorus-containing groups, there is disclosed a compound with an electrochemical potential value of in excess of 500 mV. It is believed that compounds of the invention that include sulfur-containing groups or phosphorus-containing groups, especially those in which the sulfur or phosphorus atom is directly boded to a ring carbon of the ferrocenyl, will be advantageous in extending the range of available potential values of such labels, making them useful as labels in electrochemical assays. In particular, those compounds offer the possibility of use in assays in which the high electrochemical potential value may be valuable, for example in multiplex assays where a range of different labels with differentiable electrochemical potentials are used.

In certain preferred compounds there is present as a said sulfur-containing group at least one sulfonyl substituent selected from groups of the formula $R^{15}S(O)_2$—, wherein $R^{15}$ is selected from branched- or straight-chain alkyl, haloalkyl, and substituted or unsubstituted aryl. Illustrative alkyl groups $R^{15}$ include, for example, methyl, ethyl, propyl, or butyl, especially t-butyl.

Preferred haloalkyl groups $R^{15}$ include, for example, fluoroalkyl groups with one of more fluoro substituents, especially trifluoromethyl. In certain preferred embodiments, $R^{15}$ represents unsubstituted C1 to C4 alkyl; or C1 to C4-haloalkyl, for example C1 to C4-fluoroalkyl, especially trifluoromethyl. Illustrative aryl groups $R^{15}$ include, especially, phenyl, which may be substituted or unsubstituted, with preferred substituents including, for example, halo, unsubstituted alkyl (preferably C1 to C4 alkyl), substituted alkyl (for example haloalkyl), nitro, cyano, alkoxy (for example, C1 to C4 alkoxy, preferably methoxy) and sulfur-containing groups, for example sulfonyl. Other illustrative aryl substituents $R^{15}$ include heteroaryl groups containing at least one heteroatom selected from oxygen, sulphur and nitrogen. Illustrative of preferred aryl groups R are those of general formula $(R^{16})_a$— Ar—, or $(R^{16})_a$— HeAr— in which Ar represents aryl; HeAr represents heteroaryl; $R^{16}$ is a substituent selected from halo, alkyl, nitro, cyano, haloalkyl, alkoxy, and sulphur-containing groups, for example sulfonyl; and a is an integer in the range of from 0 to a number equal to the maximum substitutable ring positions in the aryl, or heteroaryl ring. For example, $R^{15}$ may represent phenyl substituted by F; Cl; Br; I; unsubstituted C1 to C4 alkyl; C1 to C4 haloalkyl, for example trifluoromethyl; nitro; cyano; methoxy; or sulfur-containing groups, for example sulfonyl.

In further embodiments, there is present as a said phosphorus-containing substituent a group of the general formula $(R^{17})_2P(O)$—, wherein each $R^{17}$ is independently selected from branched- or straight-chain alkyl, haloalkyl, substituted or unsubstituted aryl and substituted or unsubstituted heteroaryl. Advantageously. $R^{17}$ represents C1 to C4 alkyl, which is preferably unsubstituted, for example, methyl, ethyl, propyl, or butyl, especially t-butyl.

Illustrative aryl substituents $R^{17}$ include phenyl and heteroaryl groups containing at least one heteroatom selected from oxygen, sulphur and nitrogen, each of which may be unsubstituted or substituted. Preferred aryl groups $R^{17}$ include those of general formula $(R^{18})_b$— Ar—, or $(R^{18})_b$—HeAr— in which Ar is aryl; HeAr is heteroaryl; $R^{18}$ is a substituent selected from halo, alkyl, nitro, cyano, haloalkyl, alkoxy and sulphur-containing groups, for example sulfonyl; and b is an integer in the range of from 0 to a number equal to the maximum substitutable ring positions in the aryl or heteroaryl ring. For example, $R^{17}$ may represent phenyl substituted by F, Cl, Br, I, unsubstituted C1 to C4 alkyl, C1 to C4 haloalkyl, for example trifluoromethyl, nitro, cyano, or methoxy. Preferably, Ar represents phenyl and comprises one or more substituents $R^{18}$ (which may be the same or different) selected from halo, alkyl, haloalkyl, nitro, cyano, and alkoxy. More preferably, each $R^{17}$ is the same and represents phenyl with at least one substituent, especially phenyl with one substituent in the 4-position. In one preferred embodiment, $R^{17}$ represents branched C1 to C4 alkyl, for example t-butyl.

In another advantageous embodiment the ferrocenyl groups are the same and there is present as a said substituent on each ferrocenyl at least one substituted phenyl group in which the phenyl has at least one substituent selected from halo, C1 to C4 alkyl, nitro, cyano, C1 to C4 haloalkyl, C1 to C4 alkoxy, and sulfur-containing radicals, for example, sulfonyl. Illustrative of such substituents on the phenyl are, for example, fluorine, chlorine, bromine, iodine atoms, nitro, cyano, trifluoromethyl, and methoxy. In certain embodiments, each phenyl has one substituent which may be located in the 4-position, for example, 4-nitrophenyl (wherein the ferrocenyl group is attached to the phenyl group at the 1-position).

In a further embodiment there is present as a said substituent on each ferrocenyl at least one heteroaryl group which may be unsubstituted or substituted by at least one substituent selected from halo, C1 to C4 alkyl, nitro, cyano, C1 to C4 haloalkyl and C1 to C4 alkoxy. For example, there may be present as a heteroaryl group furanyl.

In yet further embodiments, there may be present as a said substituent on each ferrocenyl at least one iodine or chlorine atom. Other possible substituents include at least one silyl substituent, preferably a silyl group selected from alkyl silyl groups, for example trialkylsilyl, especially trimethylsilyl.

In addition to at least one substituent as defined with reference to general formula I herein, each ferrocenyl moiety may optionally be further substituted by at least one additional substituent, for example, by at least one additional substituent selected from bromo, fluoro, C1 to C4-alkyl, haloalkyl, and C1 to C4 alkenyl. In accordance with a further embodiment. Fc and Fc' may each additionally comprise at least one cyano group substituent on its distal ring.

It is preferred that the ferrocenyl moieties are identical. That is thought to give a stronger signal.

The moiety Z may be unsubstituted or substituted. Substituents, when present, may be for example one or more substituents selected from hydroxy, halo, cyano, amino, and unsubstituted or substituted C1-C4 alkyl, C1-C4 alkenyl, or aryl; wherein in each case optional substituents include without limitation hydroxy, halo, cyano, oxo, amino, ester or amido. The moiety Z may, if desired, be interrupted by one, or optionally more than one, atom or moiety selected from —O—, —S—, cycloalkyl, including heterocycloalkyl, —CO—, —CONH—, —NHCO— and —NH— and —NR$^1$— in which R$^1$ is C1 to C4 alkyl. Illustrative of cycloalkyl moieties that may be included as interruptions within the moiety Z are cycloalkyl rings with from 5 to 7 ring atoms, especially 6 ring atoms, for example cyclohexyl, piperidinyl, morpholinyl.

The moieties X and Y, which are preferably the same, advantageously have a chain length of from 1 to 6, preferably from 1 to 4 carbon atoms, especially one or two carbon atoms, and more especially one carbon atom. The moieties X and Y may each represent an alkylene chain, optionally interrupted by —O—, —S— or —NR$^5$— for example —NH—. Preferred moieties X and Y include, for example, —CH$_2$—, —CH$_2$—CH$_2$—, —(CH$_2$)$_3$—O— CH$_2$—, —CH$_2$—O—(CH$_2$)$_3$—, —(CH$_2$)$_3$—O—(CH$_2$)$_2$—, and —(CH$_2$)$_2$—O—(CH$_2$)$_3$—.

In some embodiments, labels according to the present invention may be prepared by reacting two equivalents of a suitable substituted ferrocene carboxaldehyde in a suitable solvent in the presence of a reducing agent. The structure of the desired label, including the structure of moiety Z, may be determined by selection of suitable starting materials and/or routine modification of the synthesis method. In one illustrative method, for example a ferrocene derivative such as 1'-iodo ferrocene carboxaldehyde, 1'-chloro ferrocene carboxaldehyde, 1'-furanyl ferrocene carboxaldehyde or 2-tert-butyl sulphonyl ferrocene carboxaldehyde may be reacted with a suitable amine (for example, 6-aminohexan-1-ol, glycine or (aminoethoxy)ethanol)) in a suitable solvent, for example THE, in the presence of a reducing agent, for example sodium triacetoxyborohydride. When glycine is used as the amine, the resulting di-ferrocenyl glycine derivative may be further modified to generate a desired structure. For example, it may be reacted with oxalyl chloride in dichloromethane then treated with 4-(hydroxymethyl)piperidine to generate a ferrocene-substituted derivative of 2-((di-ferrocenylmethyl)amino)-1-(4-(hydroxymethyl)piperidin-1-yl)ethanone. In another embodiment, when glycine is used as the amine, the resulting di-ferrocenyl glycine derivative may be further reacted with oxalyl chloride in dichloromethane then treated with 6-aminohexan-1-ol to generate a ferrocene-substituted derivative of N,N-2-(diferrocenylmethylamino)acetyl-6-aminohexanol (also named N-(6-hydroxylhexyl)-2-((diferrocenylmethyl)amino)-acetamide). Suitable methods for synthesis of other compounds according to the invention will be apparent to those skilled in the art in the light of the disclosure herein.

Linkage to the substrate can be by any suitable linkage, typically by linkage to a substrate side chain. The linker group R in the compounds of general formula I may be any group suitable for effecting linkage to the substrate either directly or via a functionalising group as described herein. R is advantageously, although not necessarily, a linker group comprising an oxygen atom. R is preferably a hydroxyl group or a protected hydroxyl group or a group containing a hydroxyl group or a protected hydroxyl group. It will be appreciated, however, that any other suitable linker group R may be selected having regard to the substrate to which, in use, the compound is to be attached. Various synthetic methods have been developed for the derivatisation of protein, peptide or amino acid side chains or protein, peptide or amino acid terminal moieties. For example, lysine residues in a protein may be derivatised by reaction with a succinimidyl ester. For derivatisation at other amino acid residues, other known synthetic methods may be used. For example, a maleimide reagent may be used to derivatise cysteine residues. An N-hydroxy succinimide ester may be used to derivatise the amino terminus or side chain amino group of a protein or peptide, or an amino moiety of an amino acid.

Suitable derivatisation methods for nucleotides are also well-known, for example, using a phosphoramidite moiety.

The above derivatisation methods are illustrative of the methods that may be used to link the compounds of the invention to a substrate, although other methods may be used.

Labelled substrates according to the invention may be prepared by reaction of a compound according to the invention, optionally after functionalisation to obtain a functionalised labelling compound, with a substrate, for example, with a substrate selected from amino acids, nucleotides (for example oligo deoxyribonucleotides or oligo ribonucleotides), nucleosides, sugars, peptides, proteins, oligonucleotides, polynucleotides, carbohydrates and derivatives of any of those molecules.

In a preferred embodiment, the substrate is a nucleotide or an oligonucleotide. The nucleotide may be selected from adenosine, thymidine, guanosine, cytidine or uridine nucleotides.

Preferably the nucleotide, or a nucleotide of the oligonucleotide, is attached to the label through a group attached to the ribose or deoxyribose group of the nucleotide, for example in the 2', 3' or 5' position, for example through an oxygen or nitrogen atom. Most preferably, the nucleotide is attached at the 3' or 5' position, for example at the 5' position. Linking at other positions is also possible.

In the case of nucleotides, one advantageous way of attaching labels of the invention is by functionalization with phosphoramidite. The linking of phosphoramidite groups to oligonucleotides is widely practised in oligonucleotide synthesis and thus methods and conditions for attachment to an oligonucleotide of labels functionalised with phosphoramidite will be well-known and a routine matter to those skilled in the art. Further, it advantageously permits the use of standard oligo manufacturing methods.

Oligonucleotides for use in an assay in accordance with the invention are advantageously nucleotides having from 2 to 50 nucleotides, more preferably from 2 to 40 nucleotides especially from 15 to 35 nucleotides, with from 18 to 30 nucleotides being especially preferred. For some applications, shorter oligonucleotides may be useful, for example oligonucleotides with from 2 to 14 nucleotides, more preferably from 2 to 10 nucleotides.

Attachment to proteins, for example via cysteine or lysine, may be accomplished in some cases by incubation of the protein and ferrocenyl label together at room temperature in an appropriate buffer solution. Where the label is advantageously to be linked to cysteine or lysine but the substrate sequence does not contain cysteine or lysine at a suitable position the sequence may if desired be mutated to add one or more cysteine or lysine residue either as an additional residue or as a substitution for another residue. An alternative method for attachment to proteins may include biotinylation of the labels and use of commercial streptavidinated proteins (or vice versa). By way of example, the substrate may be biotinylated by any standard technique for example by use of a commercially available biotinylation kit. Biotinylated substrate will bind to strepavidin or avidin conjugated compounds such as antibodies (which are commercially and widely available).

It will however be apparent to the skilled person that similar labels may be attached to a substrate at a selected one of a number of locations by use of an appropriate labelling functional group.

In functionalised labelling compounds of the general formula II:

A-L-F            III

A-L is preferably a moiety derived from a compound according to general formula I and F is a functionalising group. Preferred functionalised labelling compounds of the general formula II include compounds of the general formula IIIb:

A-O—F            IIIb wherein A-O is a moiety derived from a compound according to general formula I, preferably by loss of a hydroxy hydrogen atom or protecting group when the linker group R of general formula I is hydroxyl or a hydroxyl-containing group or is a protected hydroxyl group, and F is a functionalising group.

Suitable functionalising groups that may be usable with labels of the invention, including as functionalising group F in general formula III and general formula IIIb, may include, without limitation, succinimidyl ester groups, phosphoramidite groups, maleimide groups, biotin and azide groups. It will be appreciated, however, that there may be used any functionalising group that facilitates attachment of the labelling compound to the substrate to be labelled.

The invention also provides a method of detecting a nucleic acid (for example RNA or DNA) in a sample comprising the optional step of amplifying the nucleic acid (for example by PCR or another nucleic acid amplification technique) followed by the step of contacting the amplicon (or the nucleic acid) with a complementary nucleic acid probe under conditions to allow hybridization between the probe and amplicon (or the nucleic acid), followed by the step of selectively degrading either hybridized or unhybridized probe (for example by use of single or double strand specific nucleases), wherein said probe is labelled with an electrochemically active compound of the invention and wherein the method provides the step of measuring the electrochemical activity of the compound labelling the probe of wherein said electrochemical activity is dependent either quantitatively or qualitatively on the extent of degradation of the probe.

The invention also provides a method of detecting an antibody or derivative (which may for example be bound to target antigen in an assay) with an electrochemically active compound of the invention comprising the step of measuring the electrochemical activity of the compound. This method can be performed quantitatively or qualitatively.

The invention also provides methods of diagnosing or monitoring a disease in a subject comprising using a method of the invention in the detection of a protease or a protease inhibitor associated with said disease in a tissue or body fluid of the subject. A substrate for the protease can be labelled according to the invention.

The invention also provides methods of diagnosing or maintaining a disease in a subject comprising using a method of the invention to detect a peptide or protein associated with said disease in a tissue or body fluid of the subject.

The invention also provides methods of diagnosing or monitoring a disease in a subject comprising using a method of the invention in the detection of a nuclease or a nuclease inhibitor associated with said disease in a tissue or body fluid of the subject.

Furthermore, the invention provides use of a method of the invention for detecting a disease in a subject.

The invention also provides methods of detecting a microorganism (in particular, a pathogen or other undesirable organism, for example a food spoilage organism), comprising using a method of the invention. A substrate from the microorganism (or derived from the pathogen e.g. a nucleic acid amplicon produced using a target nucleic acid sequence in the pathogen) can be labelled according to the invention. Detection of the labelled substrate can be used to indicate detection of the microorganism.

The invention also provides an assay comprising a step which uses a labelled substrate of the invention, optionally in combination with other assay components for example a sample vessel, a container comprising electrodes for electrochemical detection, enzymes for use in the assay or standards and controls. Said assay may use more than one different labelled substrate of the invention. If that is the case the presence of different labelled substrates may be differentially detected by labelling them with electrochemical labels of the invention having different electrochemical characteristics (for example different oxidation potentials) thereby permitting the assay to be a multiplex (for example a duplex) assay in which different substrates may be discriminated when present in the same sample vessel. Simplex assays are also encompassed by the invention.

Table 1a below sets out certain illustrative formulae of compounds according to the invention which may be used as labels in electrochemical assays in accordance with the invention, and which may be used to make functionalised labelling compounds and labelled substrates according to the invention. Table 1a also sets out in the second column illustrative corresponding functionalised labelling compounds according to the invention. Tables 1b, 2, 3 and 4 set out general formulae of further illustrative compounds of the invention. Whilst functionalised compounds corresponding to the compounds identified in Tables 1b, 2, 3 and 4 are not shown, it will be appreciated that the compounds shown may be functionalised by addition of any suitable functionalising moiety. In the formulae in Tables 1a, 1b, and 2 to 4, except where considerations of steric hindrance mitigate against it, each ferrocenyl may have more than one substituent, which may be the same or different, and in any ring position. Both ferrocenyl groups preferably have the same substituent(s) in the same positions. i.e. both ferrocenyl groups are the same.

TABLE 1a

Illustrative embodiments with cyclopentadienyl ring substituents in accordance with the invention

| | General formula of compound | General formula-illustrative functionalised label | Identification of symbols |
|---|---|---|---|
| 1 | (structure with Fc-CH₂-N(CH₂-Fc)-W-OH, with $(R^{10})_q$ substituents on cyclopentadienyl rings) | (structure with phosphoramidite: Fc-CH₂-N(CH₂-Fc)-W-O-P(O-CH₂CH₂-CN)(N(iPr)₂), with $(R^{10})_q$ substituents) | $R^{10}$ represents a radical selected from S-containing groups, P-containing groups, I, Cl, trialkylsilyl, $CF_3$, heteroaryl, substituted phenyl; q represents from 1 to 5, for example 1; and W represents $(CH_2)_n$ where n is from 0 to 6, O, S or $NR^{20}$ where $R^{20}$ is alkyl, for example C1 to C4 alkyl |
| 2 | (structure with Fc-CH₂-N(CH₂-Fc)-W-OH, with $(R^{11})_r$ substituents on cyclopentadienyl rings) | (structure with phosphoramidite: Fc-CH₂-N(CH₂-Fc)-W-O-P(O-CH₂CH₂-CN)(N(iPr)₂), with $(R^{11})_r$ substituents) | $R^{11}$ represents a radical selected from S-containing groups, P-containing groups, I, Cl, trialkylsilyl, $CF_3$, heteroaryl, substituted phenyl and cyano; r represents from 1 to 5, for example 1; and W represents $(CH_2)_n$ where n is from 0 to 6, O, S or $NR^{20}$ where $R^{20}$ is alkyl, for example C1 to C4 alkyl |

TABLE 1a-continued

Illustrative embodiments with cyclopentadienyl ring substituents in accordance with the invention

| General formula of compound | General formula-illustrative functionalised label | Identification of symbols |
|---|---|---|
| 3 | 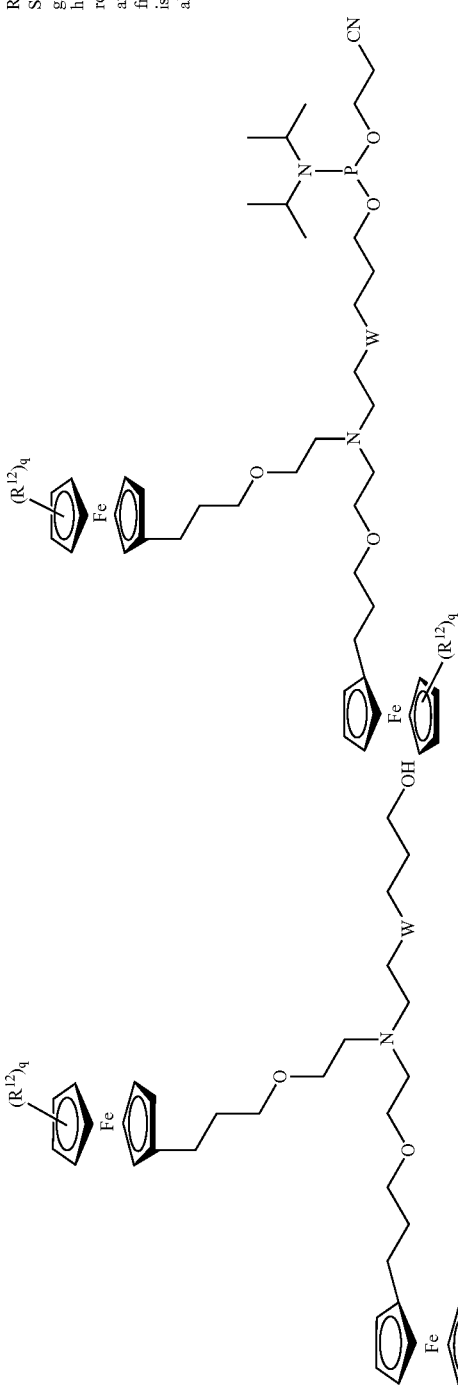 | $R^{12}$ represents a radical selected from S-containing groups, P-containing groups, I, Cl, trialkylsilyl, $CF_3$, heteroaryl, substituted phenyl; q represents from 1 to 5, for example 1; and W represents $(CH_2)_n$ where n is from 0 to 6, O, S or $NR^{20}$ where $R^{20}$ is alkyl, for example C1 to C4 alkyl |
| 4 | 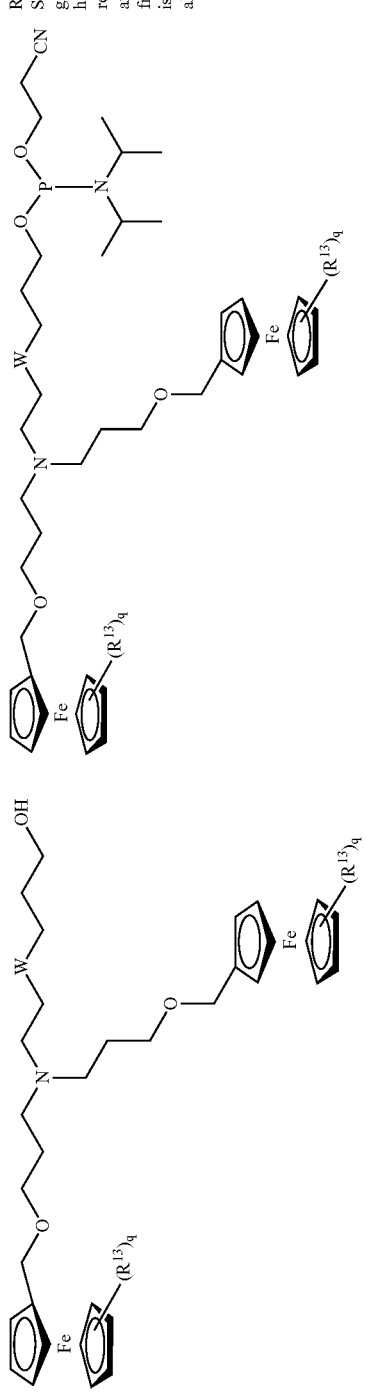 | $R^{13}$ represents a radical selected from S-containing groups, P-containing groups, I, Cl, trialkylsilyl, $CF_3$, heteroaryl, substituted phenyl; q represents from 1 to 5, for example 1; and W represents $(CH_2)_n$ where n is from 0 to 6, O, S or $NR^{20}$ where $R^{20}$ is alkyl, for example C1 to C4 alkyl |

TABLE 1a-continued

Illustrative embodiments with cyclopentadienyl ring substituents in accordance with the invention

| General formula of compound | General formula-illustrative functionalised label | Identification of symbols |
|---|---|---|
| 5 | | $R^{14}$ represents a radical selected from S-containing groups, P-containing groups, I, Cl, trialkylsilyl, $CF_3$, heteroaryl, substituted phenyl; q represents from 1 to 5, for example 1; W represents $(CH_2)_n$ where n is from 0 to 6, O, S or $NR^{20}$ where $R^{20}$ is alkyl, for example C1 to C4 alkyl; and V represents $(CH_2)_m$ where m represents from 2 to 6, optionally interrupted by an O atom |

TABLE 1b

Further illustrative embodiments with cyclopentadienyl ring substituents in accordance with the invention

| General formula of compound | Identification of symbols |
|---|---|
| 6 [structure: two ferrocenyl units with $(R^{12})_q$ substituents connected through propyl-O-ethyl chains to a central N, which bears a $-W-$propyl-OH arm] | $R^{12}$ represents a radical selected from S-containing groups, P-containing groups, I, Cl, trialkylsilyl, $CF_3$, heteroaryl, substituted phenyl, cyano; q represents from 1 to 4, for example 1; and W represents $(CH_2)_n$ where n is from 0 to 6, O, S or $NR^{20}$ where $R^{20}$ is alkyl, for example C1 to C4 alkyl |
| 7 [structure: ferrocenyl-$CH_2$-O-propyl-N(...)- with arm $-CH_2CH_2-W-$propyl-OH and a second arm $-$propyl-O-$CH_2$-ferrocenyl, each ferrocene bearing $(R^{13})_q$] | $R^{13}$ represents a radical selected from S-containing groups, P-containing groups, I, Cl, trialkylsilyl, $CF_3$, heteroaryl, substituted phenyl, cyano; q represents from 1 to 4, for example 1; and W represents $(CH_2)_n$ where n is from 0 to 6, O, S or $NR^{20}$ where $R^{20}$ is alkyl, for example C1 to C4 alkyl |
| 8 [structure: two ferrocenyl-V- groups attached to central N, with N bearing a $-CH_2CH_2-W-$propyl-OH arm, each ferrocene bearing $(R^{14})_q$] | $R^{14}$ represents a radical selected from S-containing groups, P-containing groups, I, Cl, trialkylsilyl, $CF_3$, heteroaryl, substituted phenyl, cyano; q represents from 1 to 5, for example 1; W represents $(CH_2)_n$ where n is from 0 to 6, O, S or $NR^{20}$ where $R^{20}$ is alkyl, for example C1 to C4 alkyl; and V represents $(CH_2)_m$ where m represents from 2 to 6 optionally interrupted by an O atom |

The compounds 6 to 8 above may be functionalised by any suitable method, for example by phosphoramidation analogously to the compounds 1 to 5 shown in Table 1 above.

In Table 2 below there are shown general formulae describing certain preferred embodiments of the invention in which each ferrocenyl group is substituted by a sulfonyl group. Table 3 below shows general formulae describing certain preferred embodiments of the invention in which each ferrocenyl group is substituted by a phosphinyl group. The compounds in Tables 2 and 3 may each be functionalised by any suitable method, for example phosphoramidation. The present invention encompasses the functionalised analogs of the compounds defined in the Tables 1a, 1b, 2 and 3 as well as labelled substrates derived therefrom.

TABLE 2
Illustrative embodiments with sulfonyl radicals as cyclopentadienyl ring substituents
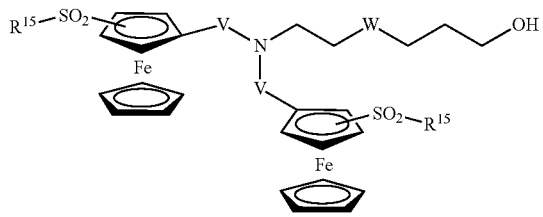
9.
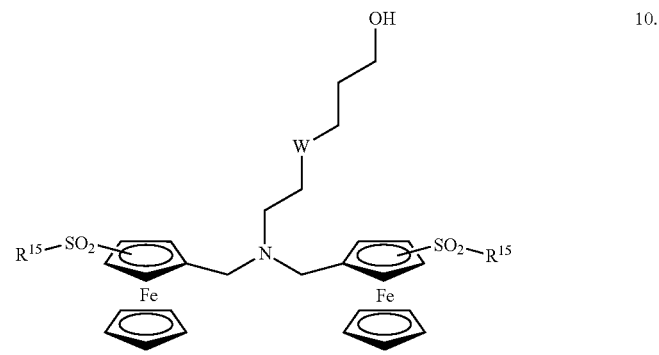
10.
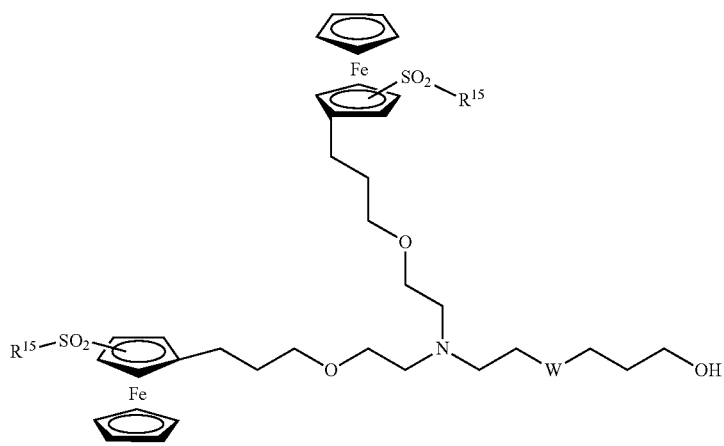
11.
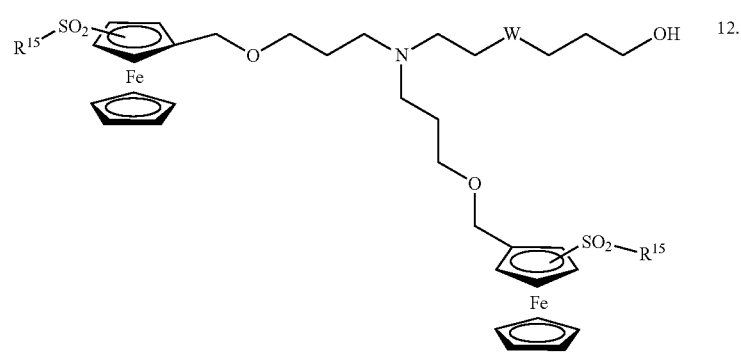
12.
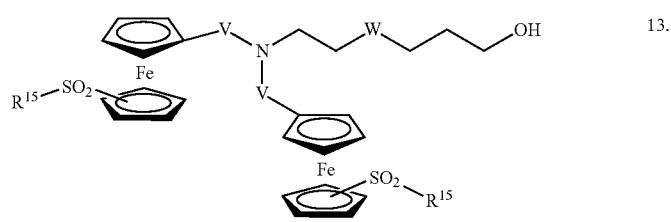
13.

TABLE 2-continued
Illustrative embodiments with sulfonyl radicals as cyclopentadienyl ring substituents
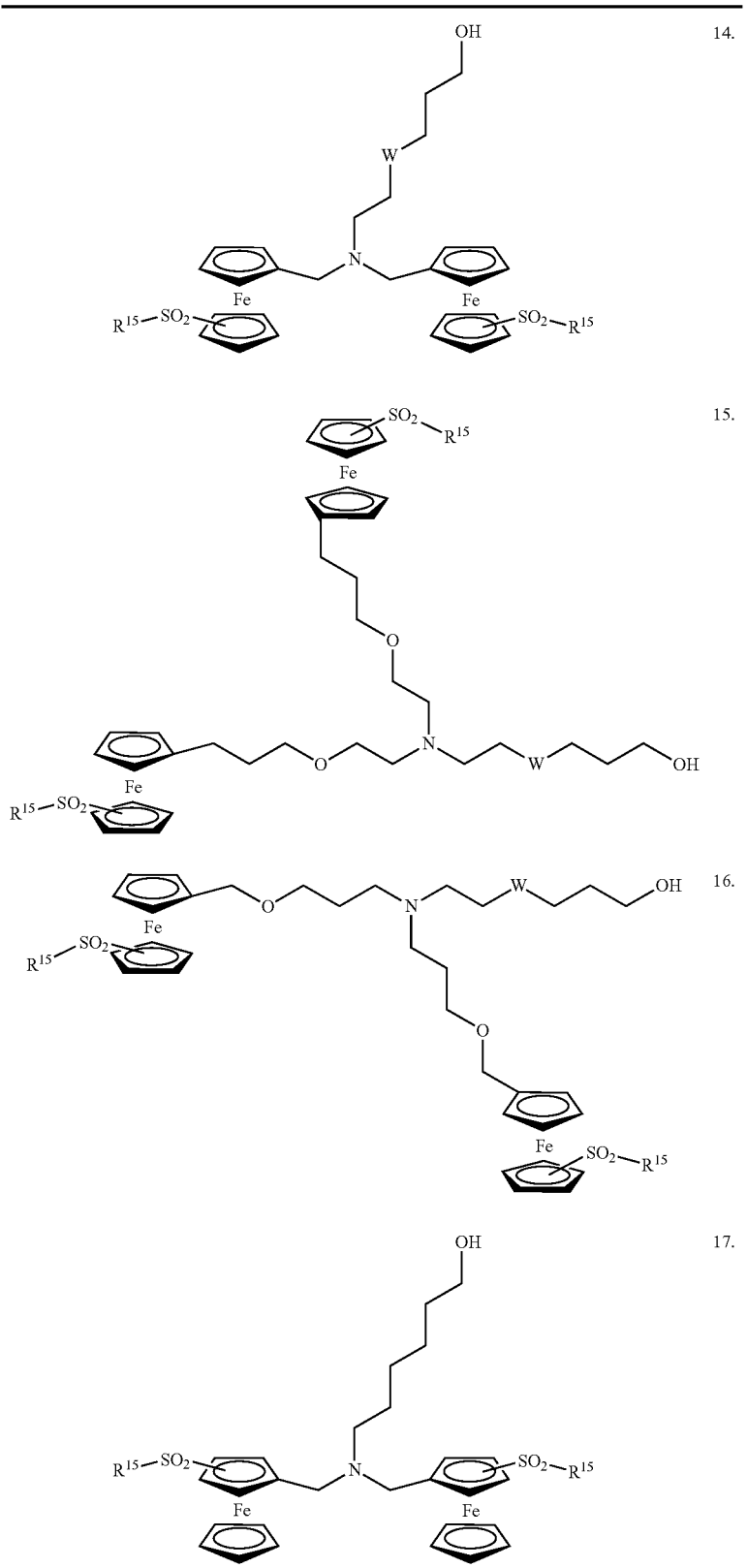

TABLE 2-continued

Illustrative embodiments with sulfonyl radicals as cyclopentadienyl ring substituents 18.
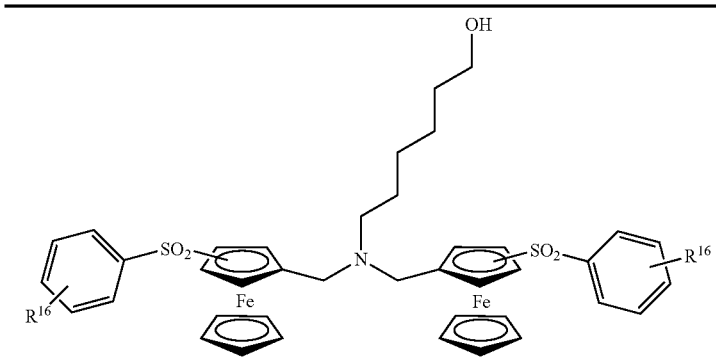

19.
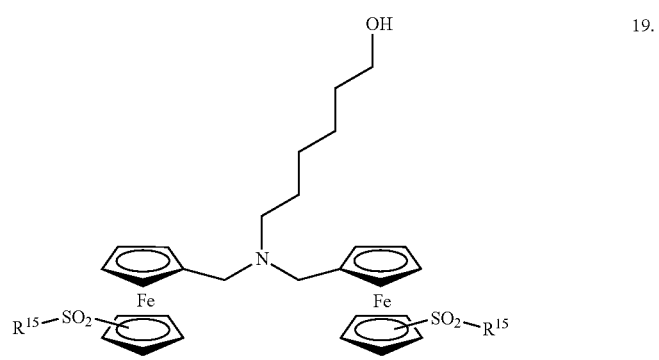

20.
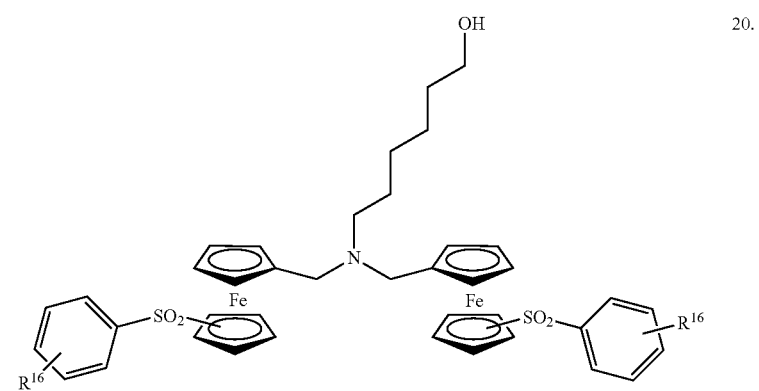

Where present in the formulae 9 to 20 above:

$R^{15}$ represents alkyl, for example t-butyl, haloalkyl, especially fluoroalkyl, for example $CF_3$, phenyl or substituted phenyl;

W represents $(CH_2)_n$ where n is from 0 to 6, O, S or $NR^{20}$ where $R^{20}$ is alkyl, for example C1 to C4 alkyl; and V, where present, represents $(CH_2)_m$ where m represents from 2 to 6, optionally interrupted by an O atom; and $R^{16}$, where present, represents one or more radicals selected from F, Cl, Br, I, alkyl, $NO_2$, cyano, $CF_3$ and methoxy.

TABLE 3
Illustrative embodiments with phosphinyl radicals as cyclopentadienyl ring substituents
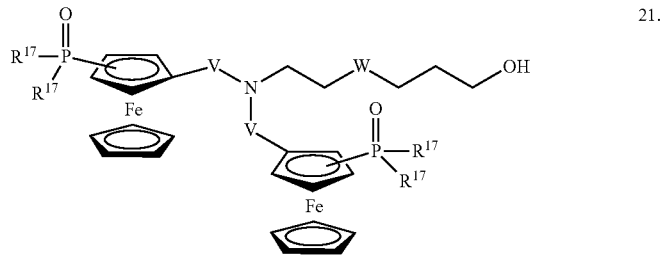
21.
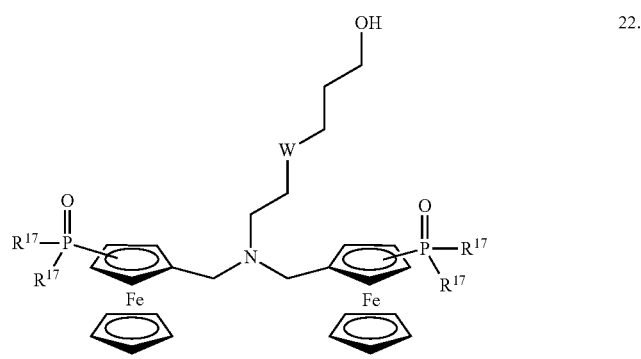
22.
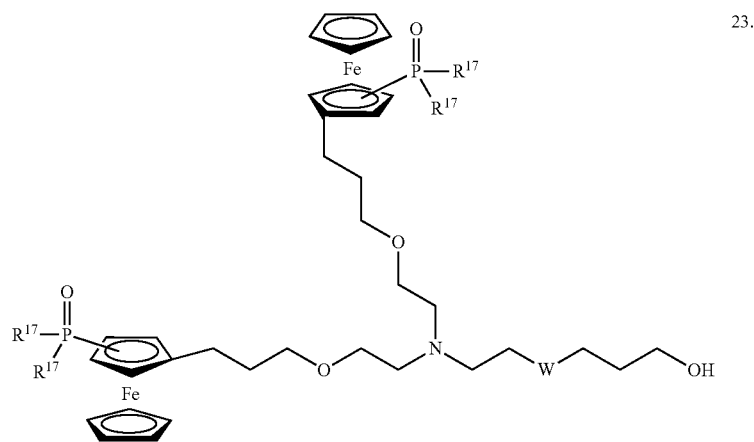
23.
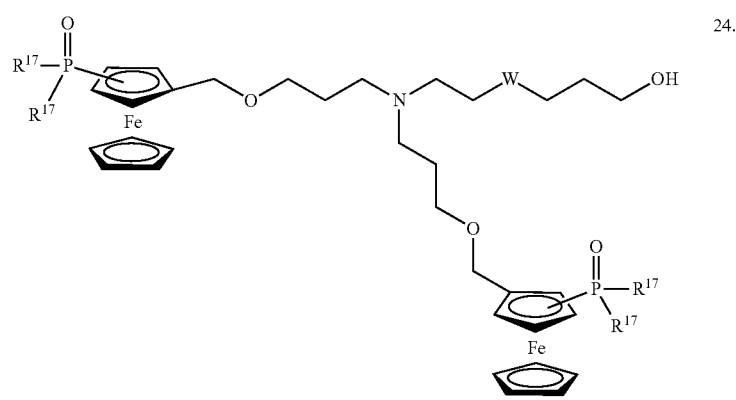
24.

TABLE 3-continued
Illustrative embodiments with phosphinyl radicals as cyclopentadienyl ring substituents
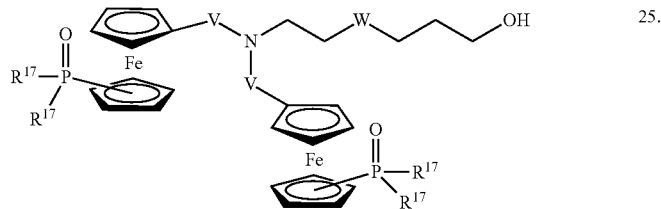 25.
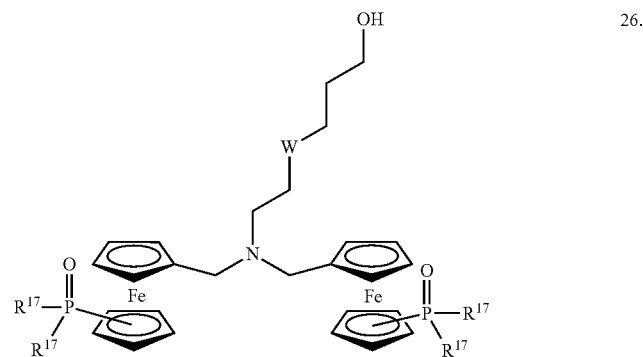 26.
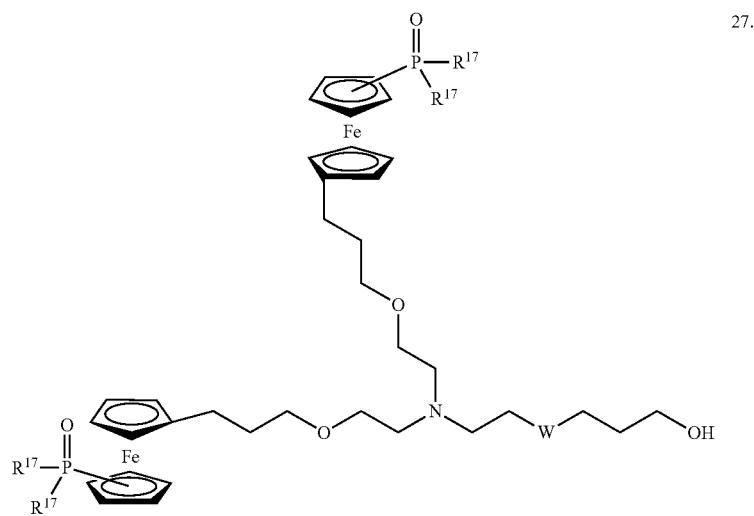 27.
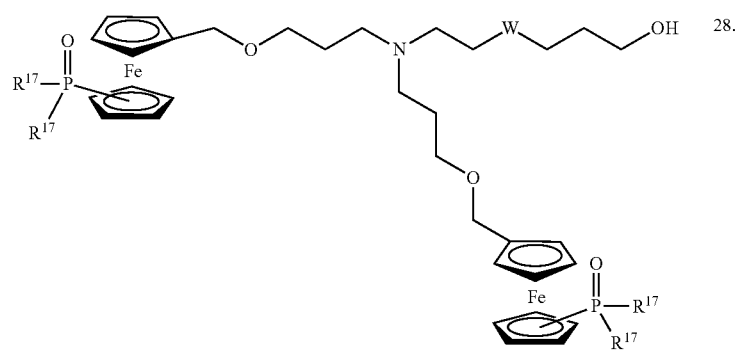 28.

TABLE 3-continued
Illustrative embodiments with phosphinyl radicals as cyclopentadienyl ring substituents
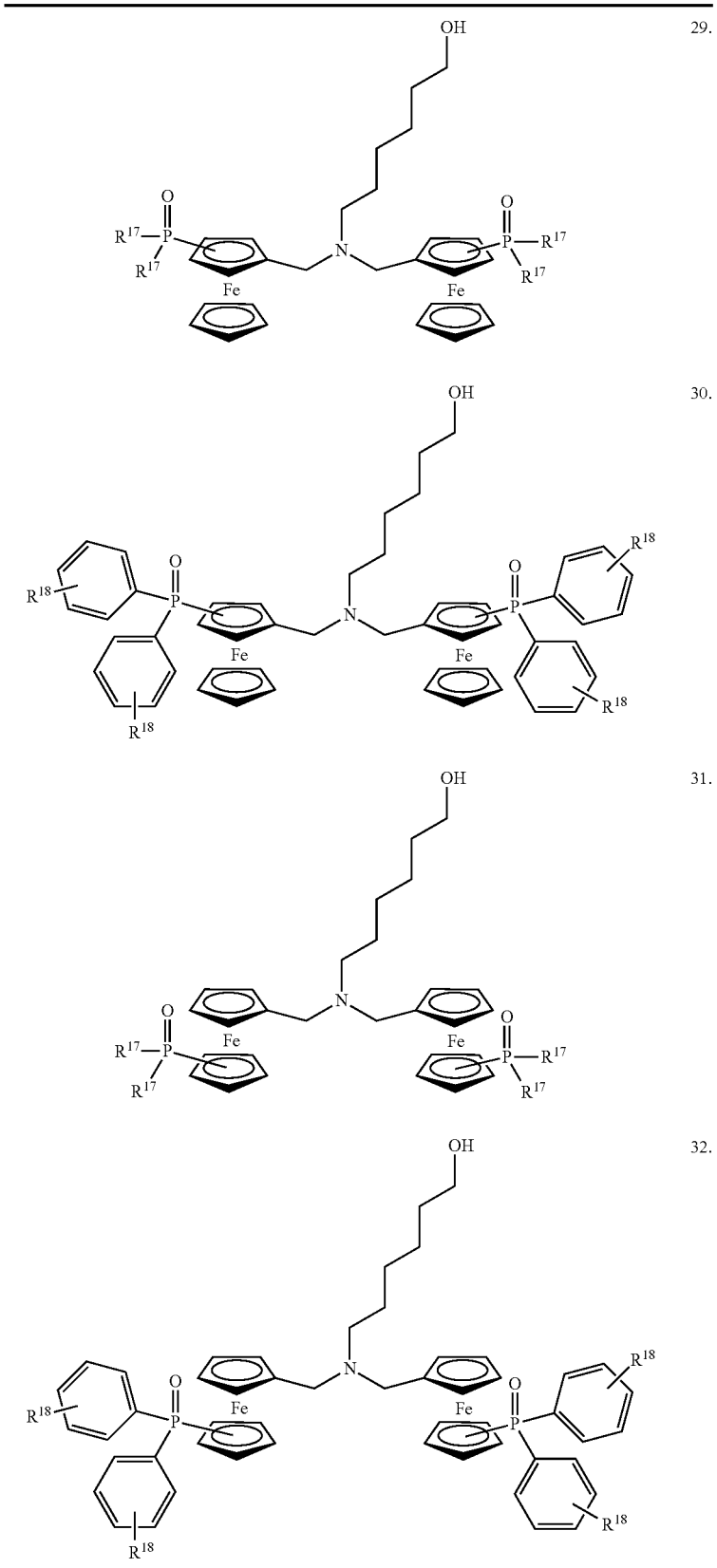
29.
30.
31.
32.

Where present in the respective formulae 21 to 32 above:

- $R^{17}$ represents alkyl, for example t-butyl, phenyl or substituted phenyl;
- W represents $(CH_2)_n$ where n is from 0 to 6, O, S or $NR^2$ where $R^{20}$ is alkyl, for example C1 to C4 alkyl;
- V represents $(CH_2)_m$ where m represents from 2 to 6, optionally interrupted by an O atom; and
- $R^{18}$ represents one or more radicals selected from F, Cl, Br, I, alkyl, $NO_2$, cyano, $CF_3$ and methoxy; in an especially preferred embodiment, $R^{18}$ represents one of said radicals and is located in the 4-position.

In the general formulae and their functionalised counterparts in Tables 1a, 1b, 2 and 3 when one or more ring substituents is present on the proximal pentadienyl ring of each ferrocenyl, that is, the ring that is directly bonded to the rest of the molecule, there is preferably a said ring substituent at an adjacent ring position to that bond. When more than one ring substituent is present on each proximal pentadienyl ring, those substituents may be in any position relative to one another. When more than one ring substituent is present on each distal pentadienyl ring of each ferrocenyl, that is, the ring remote from the bond linking the ferrocenyl to the rest of the molecule, those substituents may be in any position relative to one another. Whilst in the compounds shown in the above Tables there are shown ring substituents on either the proximal or the distal ring, it is also possible for both pentadienyl rings of each ferrocenyl to carry one or more substituents.

As illustrated in the Examples herein, incorporation of one or more substituents on each of the ferrocenyl groups (the substituents on each ferrocenyl being the same) can be used to obtain compounds with modified electrochemical characteristics, providing through appropriate substituent selection a suite of compounds from which two or more may be selected for the purpose of multiplex reactions.

Certain illustrative compounds according to the invention which have been found to have good electrochemical properties are set out in Table 4 below. The invention includes in addition to the compounds in Table 4 functionalised labelling compounds and labelled substrates which are derivable from those compounds in accordance with the invention.

TABLE 4

Illustrative labelling compounds according to the invention

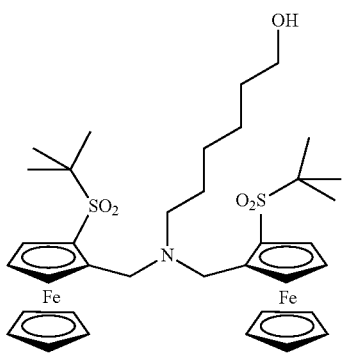

6-(bis((2-tert-butyl-sulfonylferrocenyl)1-methylferrocenyl)amino)hexan-1-ol

TABLE 4-continued

Illustrative labelling compounds according to the invention

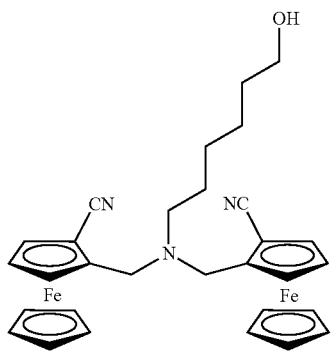

6-(bis((2-cyanoferrocenyl)1-methylferrocenyl)amino)hexan-1-ol

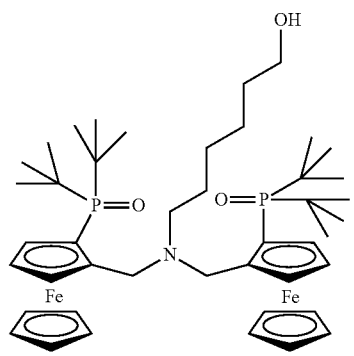

6-(bis((2-di-tert-butyl-phosphinyl-ferrocenyl)1-methylferrocenyl)amino)hexan-1-ol

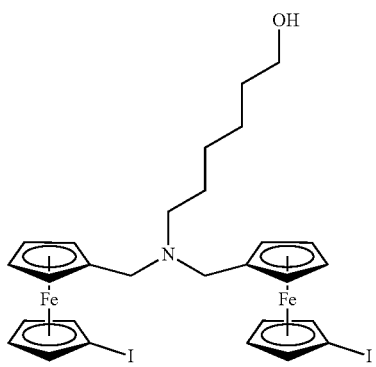

6-(bis((1'-iodoferrocenyl)1-methylferrocenyl)amino)hexan-1-ol

TABLE 4-continued

Illustrative labelling compounds according to the invention

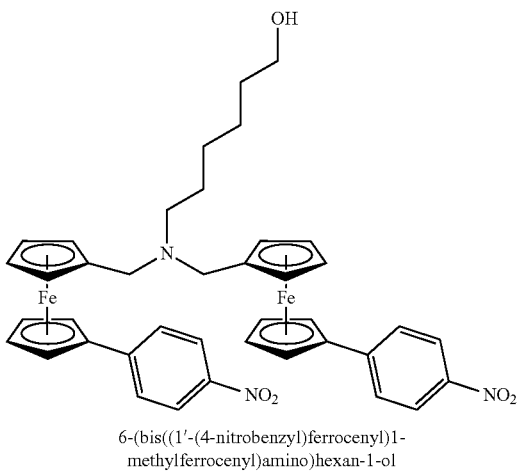

6-(bis((1'-(4-nitrobenzyl)ferrocenyl)1-methylferrocenyl)amino)hexan-1-ol

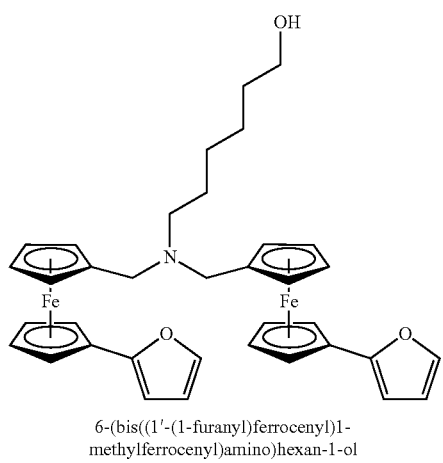

6-(bis((1'-(1-furanyl)ferrocenyl)1-methylferrocenyl)amino)hexan-1-ol

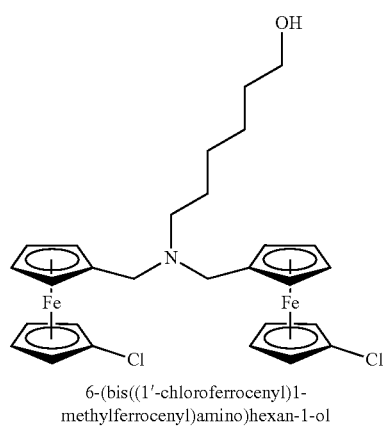

6-(bis((1'-chloroferrocenyl)1-methylferrocenyl)amino)hexan-1-ol

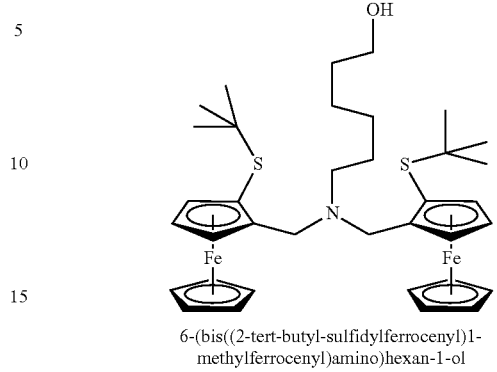

6-(bis((2-tert-butyl-sulfidylferrocenyl)1-methylferrocenyl)amino)hexan-1-ol

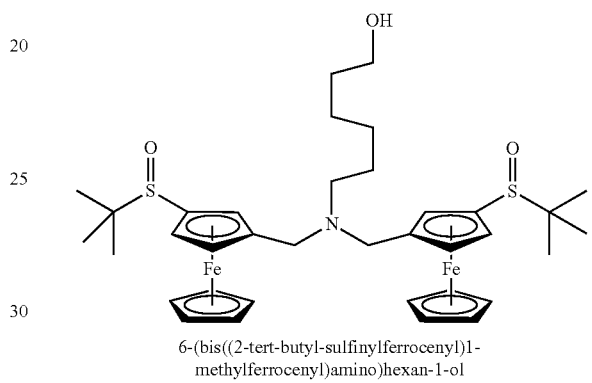

6-(bis((2-tert-butyl-sulfinylferrocenyl)1-methylferrocenyl)amino)hexan-1-ol

DETAILED DESCRIPTION OF CERTAIN PREFERRED EMBODIMENTS

The following examples illustrate compounds of the invention wherein Fc and Fc' are the same:

Materials and Methods

1'-Iodo ferrocene carboxaldehyde was synthesised from iodoferrocene using the method described in *Organometallics*, 2011, 30, 3504-3511.

1'-Furanyl ferrocene carboxaldehyde was synthesised from 1'-iodoferrocene carboxaldehyde, using method adapted from *Angewandte Chemie*, 2006, 45, 1282-1284.

1-[(Dimethylamino)methyl]-2-(di-tert-butyl phosphinyl)-ferrocene was synthesised from dimethylaminomethyl ferrocene using method adapted from *Organometallics*, 1985, 7 1297-1302.

1'-Chloro ferrocene carboxaldehyde was prepared from chloroferrocene using the procedure from *Coll. Chechoslovak. Chemm. Commun.*, 1987, 52, 174-181.

2-tert-Butyl sulphonyl ferrocene carboxaldehyde was obtained from synthesised from dimethylaminomethyl ferrocene using method adapted from *Organometallics*, 1985, 7, 1297-1302.

2-Cyanoethyldiisopropylchlorophosphoramidite was obtained from Sigma-Aldrich.

6-(Bis((2-formyl)1-methylferrocenyl)amino)hexan-1-ol was synthesised from (+/−)-4-(methoxymethyl)-2-ferrocenyl-1,3-dioxane using a method adapted from *Journal of Organic Chemistry*, 1997, 62, 6733-6745.

Iodoferrocene was synthesised from ferrocene, from an adaptation of the method described in *Journal of Organometallic Chemistry*, 2011, 696, 1536-1540, utilising iodine as a suitable electrophile.

Chloroferrocene prepared from ferrocene using a modified procedure from *J. Organomet. Chem.*, 1996, 512, 219-224, using hexachloroethane as a chlorinating reagent.

6-Aminohexanol, ferrocene, dimethylaminomethyl ferrocene and 4-nitrobenzene boronic acid were obtained from Sigma-Aldrich.

1-[(Dimethylamino)methyl]-2-(t-butylthio)-ferrocene was prepared using the procedure from *Organomet.*, 1988, 7, 1297-1302.

3-tert-butylsulfinyl ferrocene carboxaldehyde was prepared according to the procedure described in *Chem. Commun.*, 2004, 598-599.

Determination of Electrochemical Potential

The electrochemical potential values mentioned hereafter were measured using an electrochemical cell including as background electrolyte an aqueous 100 mM solution of sodium chloride, using a printed carbon working electrode, a printed carbon counter electrode and a silver/silver chloride reference electrode, all with silver connectors. The electrodes were ink based and were screen printed on to a polymer substrate (for example Mylar) followed by heat curing. By way of illustration, the sample may be prepared as follows: Ferrocenyl label precursor (0.2 ng) is dissolved in DMSO (mL). An aliquot of 10 μL is taken of this solution and is then further diluted in the buffer (500 μL). Then an aliquot (20 μL) is applied to the screen printed electrode to run the electrochemical scan. An illustrative form of suitable cell is described and shown schematically in WO2012/085591.

Example 1—Synthesis of 6-(bis((1'-iodoferrocenyl)1-methylferrocenyl) amino)hexan-1-ol

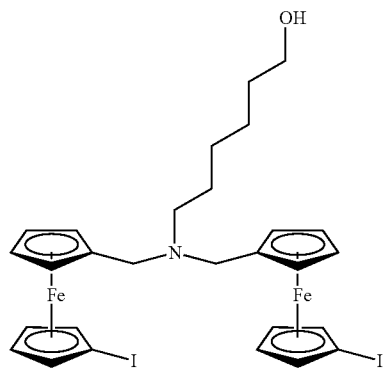

1'-Iodo ferrocene carboxaldehyde (259 mg, 0.76 mmol) was dissolved in dry THF (7 cm³) and treated with 6-aminohexan-1-ol (44 mg, 0.38 mmol) and sodium trisacetoxyborohydride (313 mg, 1.91 mmol) successively. The solution was allowed to stir at room temperature overnight. After this time the reaction was quenched by addition of NaHCO₃ (sat) (10 cm³). The organic layer was separated, then the aqueous layer back extracted with EtOAc (3×10 cm³). Combined organic extracts were dried over MgSO₄, filtered then concentrated in vacuo to give an orange oil. Product was purified by silica chromatography, eluting with 1:1 (EtOAc: Hexane)+1% NH₃OH. To give the desired product as an orange oil 123 mg, 42%. $^1$H NMR (300 MHz; d$_6$-benzene) $\delta_H$: 4.28 (4H, t, J 1.8, F$_c$H), 4.14 (4H, t, J 1.5, F$_c$H), 4.11 (4H, t, J 1.5, F$_c$H), 4.06 (4H, t, J 1.8, F$_c$H), 3.60 (2H, t, J 6.6, CH$_2$O), 3.41 (4H, s, F$_c$CH$_2$N), 2.27 (2H, t, J 7.4, NCH$_2$), 1.55-1.23 (8H, m, CH$_2$); $^{13}$C NMR (75 Mhz; d$_6$-benzene) $\delta_C$: 85.2, 75.1, 73.3, 70.9, 69.4, 62.98, 52.02, 51.8, 40.5, 32.7, 27.1, 27.0, 25.5; HRMS (ESI) m/z calcd for C$_{28}$H$_{33}$NOFe$_2$I$_2$ 765.9428, m/z found 765.9460.

The electrochemical potential was measured and found to be 442 mV.

Example 2—Synthesis of 6-(bis((1'-(4-nitrophenyl) ferrocenyl)1-methylferrocenyl) amino)hexan-1-ol

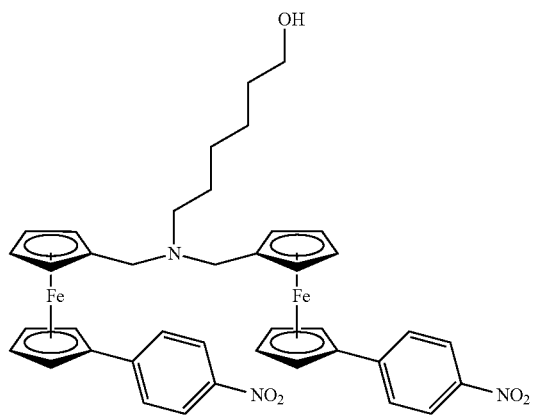

To a Schlenk tube was added 4-nitrobenzene boronic acid (39.6 mg, 0.23 mmol), trisdibenzylideneacetone palladium (Pd$_2$(dba)$_3$—1.9 mg, 2 mol %), tricyclohexylphosphine (1.4 mg, 4.8 mol %). The flask was sealed and evacuated and back filled with argon four times. The 6-(bis((1'-iodoferrocenyl)1-methylferrocenyl)amino)hexan-1-ol (83 mg, 0.11 mmol) in 1,4-dioxane (2 cm³) was then added to the flask. This was then followed by 1.27 M K$_3$PO$_4$ (aq) (141 μl, 0.18 mmol). The flask was then heated at 100° C. overnight. After this time the reaction was allowed to cool to room temperature then diluted with EtOAc (5 cm³) and H$_2$O (5 cm³). The organic layer was separated and the aqueous layer back extracted with EtOAc (3×5 cm³). The combined organics were then washed with brine (sat) (10 cm³), dried over Na$_2$SO$_4$, filtered and concentrated in vacuo to give a purple solid. Product was purified by silica chromatography, eluting with EtOAc+1% NH$_3$OH to give the desired product as an amorphous solid 11 mg, 13%.

$^1$H NMR (300 Mhz; d$_6$-benzene) $\delta_H$:8.05 (4H, app d, J 8.9, ArH), 7.08 (4H, app t, J 8.9, ArH), 4.39 (4H, t, J 1.8, F$_c$H), 4.24 (4H, t, J 1.8, F$_c$H), 3.96 (4H, t, J 1.8, F$_c$H), 3.88 (4H, t, J 1.8, F$_c$H), 3.52 (2H, t, J 5.8, CH$_2$OH), 3.01 (4H, s, CH$_2$F$_c$), 2.28 (2H, t, J 6.9. NCH$_2$), 1.50-1.26 (8H, m, CH$_2$).

The electrochemical potential was measured and found to be 437 mV.

Example 3—Synthesis of 6-(bis((1'-(1-furanyl)ferrocenyl)1-methylferrocenyl) amino)hexan-1-ol

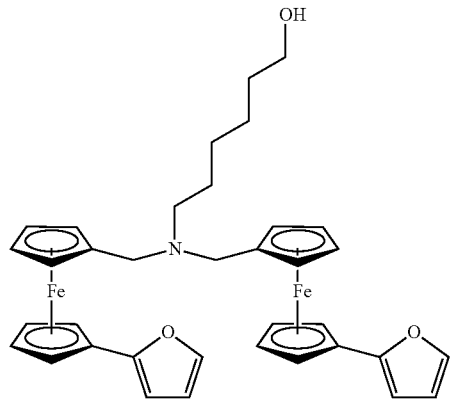

1'-Furanyl ferrocene carboxaldehyde (34 mg, 0.12 mmol) was dissolved in dry THF (1 cm³) and treated with 6-amino-hexan-1-ol (7 mg, 0.06 mmol) and sodium trisacetoxyborohydride (49 mg, 0.3 mmol) successively. The solution was allowed to stir at room temperature overnight. After this time the reaction was quenched by addition of NaHCO₃ (sat) (5 cm³). The organic layer was separated, then the aqueous layer back extracted with EtOAc (3×5 cm³). Combined organic extracts were dried over MgSO₄, filtered then concentrated in vacuo to give an orange oil. Product was purified by silica chromatography, eluting with 1:1 (EtOAc: Hexane)+1% NH₃OH to give the desired product as an orange oil 15 mg, 39%. $^1$H NMR (300 Mhz; d$_6$-benzene) δ$_H$: 7.26 (2H m, ArH), 6.25 (2H, dd, J 6.5, 1.8, ArH), 6.20 (2H, dd, J 6.5, 0.7, ArH), 4.61 (4H, t, J 1.9, F$_c$H), 4.21 (4H, t, J 1.9, F$_c$H), 4.12 (4H, t, J 1.9, F$_c$H), 4.05 (4H, t, J 1.9, F$_c$H) 3.44 (2H, t, J 6.3, CH₂OH), 3.35 (4H, s. CH₂F$_c$), 2.40 (2H, t, J 7.2, CH₂N), 1.56-1.27 (8H, m, CH₂), $^{13}$C NMR (75 Mhz; d$_6$-benzene) δ$_C$: 154.2, 141.6, 111.9, 104.4, 86.1, 77.8, 72.2, 69.6, 66.5, 63.03, 52.4, 33.5, 27.9, 27.63, 26.3, HRMS (ESI) m/z calcd for C₃₆H₃₉Fe₂NO₃ 668.15264 m/z found 668.1558.

The electrochemical potential was measured and determined to be 339 mV.

Example 4: Synthesis of 6-(bis((2-di-tert-butyl-phosphinyl-ferrocenyl)1-methylferrocenyl)amino) hexan-1-ol 6-(bis((2-di-tert-butyl-phosphinyl-ferrocenyl)1-methyl-ferrocenyl)amino)hexan-1-ol was synthesised as shown in the scheme below.

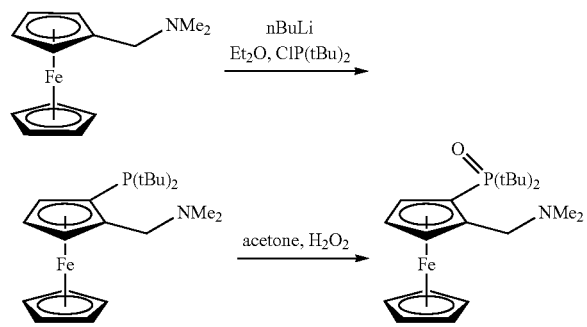

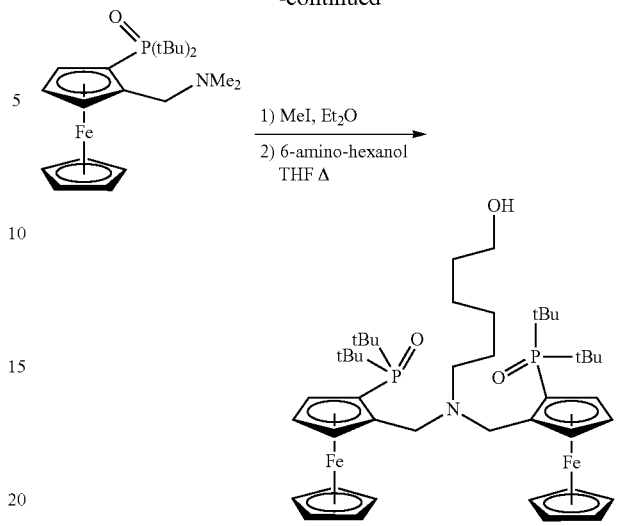

To a solution of 1-[dimethylamino)methyl]-2-(di-tert-butyl phosphinyl)-ferrocene (0.145 mg, 0.3 mmol) in diethyl ether (5 cm³) was added methyl iodide (111 µl, 1.7 mmol). The orange solution was allowed to stir at room temperature under N₂ for 1 hour. The orange suspension that was formed was then concentrated in vacuo to give a bright orange solid. The bright orange solid was then taken up in dry acetonitrile (3 cm³) and then treated with 6-amino-hexan-1-ol (17.5 mg, 0.15 mmol). The flask was then sealed and heated at reflux for 18 hours. After this time the dark orange solution was allowed to cool to room temperature. The reaction was partitioned between CH₂Cl₂ (5 cm³) and NaHCO₃ (sat) (5 cm³), the organic layer was separated and then dried over Na₂SO₄, filtered and then concentrated under reduced pressure to give a brown oil. Purification by basic alumina chromatography eluting with 2% MeOH:CH₂C2 gave the desired product as an orange oil (8 mg, 7% yield)

$^1$H NMR (250 MHz; d$_6$-benzene) δ$_H$ 4.63 (2H, app s, F$_c$H), 4.14 (12H, s, F$_c$), 3.85 (6H, br s, F$_c$H+F$_c$NCH₂), 3.55 (2H, app s. OCH₂), 2.45 (2H, app s, CH₂N), 1.47-0.95 (44H, m, tBu+CH₂), $^{31}$P NMR (121 MHz; d$_6$-benzene) δ$_P$ 61.3, HRMS (ESI µTOF) m/z calcd for C₄₄H₆₉NO₃Fe₂P₂ 834.3529 m/z found 834.3603.

The electrochemical potential (DPV) was measured and found to be 512 mV.

Example 5: 6-(bis((1'-chloroferrocenyl)1-methylferrocenyl)amino)hexan-1-ol 6-(bis((1'-chloroferrocenyl)1-methylferrocenyl)amino) hexan-1-ol was synthesised as shown in the scheme below.

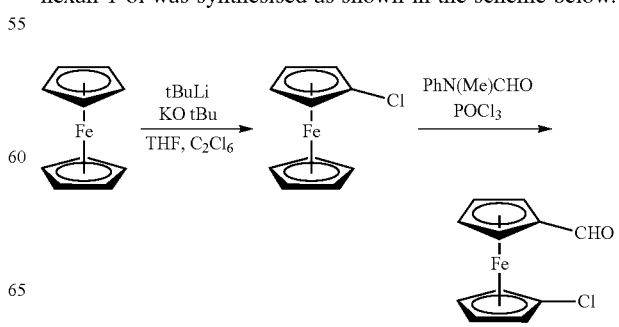

-continued

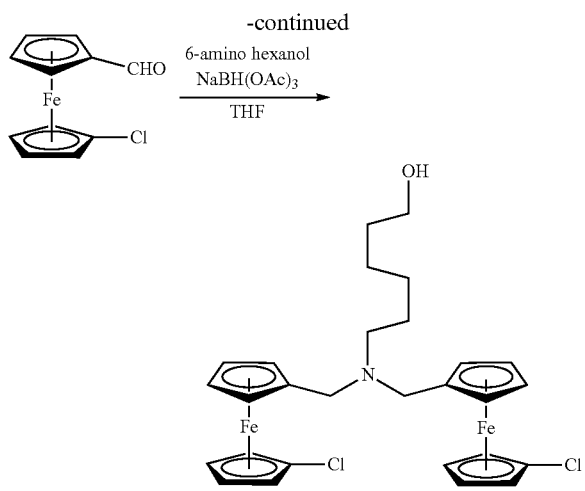

1'-chloro ferrocene carboxaldehyde (1.35 g, 5.44 mmol) was dissolved in dry THF (50 cm³) and treated with 6-aminohexan-1-ol (318 mg, 2.72 mmol) and sodiumtrisacetoxyborohydride (1.11 g, 6.80 mmol) successively. The solution was allowed to stir at room temperature overnight. After this time the reaction was quenched by addition of NaHCO₃ (sat) (30 cm³). The organic layer was separated, then the aqueous layer back extracted with EtOAc (3×30 cm³). Combined organic extracts were dried over MgSO₄, filtered then concentrated in vacuo to give an orange oil. Product was purified by silica chromatography, eluting with 1:1 (EtOAc:Hexane)+1% NH₃OH to give the desired product as an orange oil 892 mg, 56%.

$^1$H NMR (300 MHz; d₆-benzene) $\delta_H$ 4.18 (4H, t, J 1.6, F$_a$H), 4.14 (4H, t, J 1.8, F$_c$H), 3.98 (4H, t, J 1.6, F$_a$H), 3.65 (4H, t, J 1.8, F$_c$H), 3.65 (4H, s, NCH₂, F$_c$CH₂N), 3.34 (2H, t, J 6.3, OCH₂), 2.41 (2H, t, J 7.0, NCH₂), 1.55-1.23 (8H, m, CH₂), $^{13}$C NMR (75 MHz; d₆-benzene) $\delta_C$ 93.4, 86.6, 72.9, 70.6, 69.1, 68.1, 67.3, 63.0, 52.8, 33.6, 28.1, 27.7, 26.3, HRMS (ESI µTOF) m/z calcd for C₂₈H₃₃NOFe₂Cl₂ 582.0716 m/z found 582.0722.

The electrochemical potential (DPV) was measured and found to be 452 mV.

Example 6: 6-(bis((2-cyano)1-methylferrocenyl)amino)hexan-1-ol

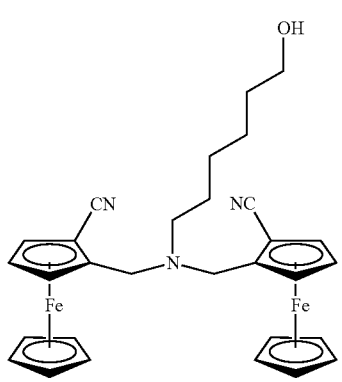

6-(bis((2-formyl)1-methylferrocenyl)amino)hexan-1-ol (1 eq) is dissolved in ethanol and treated with hydroxylamine hydrochloride (5 eq) and sodium acetate (5 eq). The resulting suspension is then heated at reflux for 18 hrs. After this time the reaction is allowed to cool to room temperature and concentrated in vacuo. The solid residue is then partitioned between chloroform and NaHCO₃ (sat). The organic layer is separated and dried over Na₂SO₄, filtered and concentrated in vacuo to give the corresponding oxime. The oxime is then taken up in dry THF and treated with (benzotriazol-1-yloxy)tris(dimethylamino)phosphonium hexafluorophosphate (BOP—2 eq) and stirred for 5 mins. Then 1,8-diazabicyclo[5.4.0]undec-7-ene (2.3 eq) is added. The solution is then stirred for 90 mins. The reaction is then diluted with EtOAc and washed with water and brine (sat). The organic phase is dried over MgSO₄, filtered and then concentrated in vacuo.

Example 7: 6-(bis((2-tert-butyl-sulfonylferrocenyl)1-methylferrocenyl)amino)hexan-1-ol

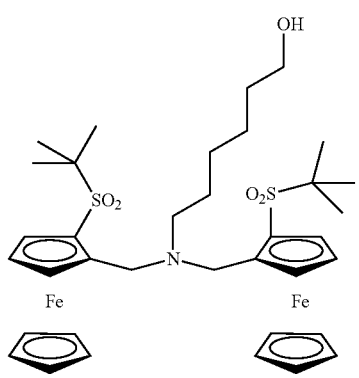

2-tert-Butyl sulphonyl ferrocene carboxaldehyde (1 eq) is dissolved in dry THF and treated with 6-aminohexan-1-ol (0.5 eq) and sodium trisacetoxyborohydride (2.5 eq) successively. The solution is allowed to stir at room temperature overnight. After this time the reaction is quenched by addition of NaHCO₃ (sat). The organic layer is separated, then the aqueous layer back extracted with EtOAc. Combined organic extracts are dried over MgSO₄, filtered then concentrated in vacuo.

Example 8: 6-(bis((2-tert-butyl-sulfulylferrocenyl)1-methylferrocenyl)amino)hexan-1-ol 6-(bis((2-tert-butyl-sulfidylferrocenyl)1-methylferrocenyl)amino)hexan-1-ol was synthesised as shown in the scheme below.

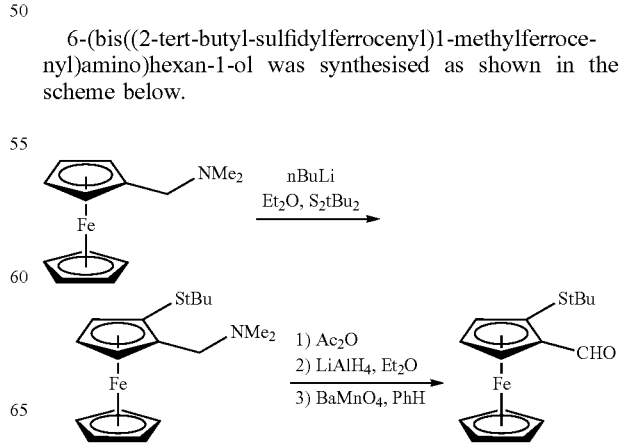

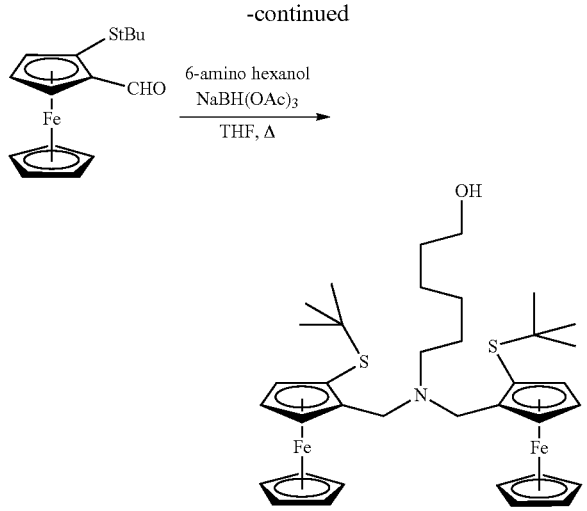

1-[(Dimethylamino)methyl]-2-(t-butylthio)-ferrocene (1.21 g, 3.49 mmol) was dissolved in acetic anhydride (10 cm). The brown solution was then refluxed for 1 hour, TLC at this indicated full consumption of the starting material. The solution was allowed to cool to room temperature, the solution was then concentrated in vacuo to approximately 90% of original volume. The resulting brown oil was then taken up in EtOAc (25 cm$^3$) and washed with NaHCO$_3$ (sat) (20 cm$^3$) and brine (sat) (20 cm$^3$). The brown solution was then dried over MgSO$_4$, filtered and concentrated in vacuo to give the desired acetoxy ester as a orange/brown oil (1.12 g, 93%) without need for further purification.

$^1$H NMR (250 MHz, C$_6$D$_6$) δ 5.37 (2H, d, J=1.43 Hz), 4.51 (1H, dd, J=2.6, 1.4), 4.44 (1H, dd, J=2.6, 1.4), 4.07 (1H, t, J=2.6), 4.07 (5H, s) 1.82 (s, 3H), 1.33 (9H, s).

To a suspension of lithium aluminium hydride (369 mg, 9.71 mmol) in Et$_2$O (15 cm$^3$) at 0° C. was added the acetoxy ester (1.12 g, 3.23 mmol) dropwise via syringe. Once addition was complete the slurry was allowed to warm to room temperature and stir for 30 mins. After this time the flask was cooled to 0° C., and then quenched by sequential addition of H$_2$O (369 μl), followed by 15% NaOH (aq) (369 μl) and H$_2$O (1.1 cm$^3$) the suspension was then allowed to warm to room temperature stirred for 10 minutes, filtered and concentrated in vacuo to the desired product as an orange solid (790 mg, 80%) without the need for further purification.

$^1$H NMR (250 MHz, C$_6$D$_6$) δ 4.64 (2H, s), 4.41 (1H, dd, J=2.4, 1.5 Hz), 4.32 (1H, dd, J=2.4, 1.5 Hz), 4.17 (5H, s), 4.08 (1H, t, J=2.6 Hz), 1.28 (9H, s).

1-tert-butyl sulfidyl-2-hydroxymethyl ferrocene (304 mg, 1 mmol) and barium manganate (1.02 g, 4 mmol) was placed in a schelnk tube, the flask sealed, then evacuated and back filled with argon four times and finally left over an Argon atmosphere. The flask was then charged with benzene (15 cm$^3$) and the slurry was allowed to stir at room temperature overnight. The slurry was then filtered through celite, and washed with Et$_2$O until the washing ran clear. The orange solution was concentrated in vacuo to give the desired product as a red oil (239 mg, 79%) without the need for further purification.

$^1$H NMR (250 MHz, C$_6$D$_6$) δ 10.69 (1H, s), 5.08 (1H, dd, J=2.5, 1.3 Hz), 4.47 (1H, dd, J=2.5, 1.3 Hz), 4.27 (1H, t, J=2.5 Hz), 4.13 (5H, s), 1.17 (9H, s).

The 2-tert-butylsulfidyl-ferrocene carboxaldehyde (237 mg, 0.78 mmol) was placed in a round bottomed flask with 6-amino-hexanol (46 mg, 0.39 mmol) and dissolved in dry THF (5 cm$^3$). The suspension was then treated with sodium trisacetoxyborohydride (322 mg, 1.96 mmol). The flask was equipped with a condenser and refluxed overnight. After this time the flask was allowed to cool to room temperature. The reaction was quenched by addition of NaHCO$_3$ (sat) (10 cm$^3$). Organics were separated and the aqueous layer back extracted with EtOAc (3×5 cm$^3$). Combined organics were washed with brine (sat) (10 cm$^3$), dried over MgSO$_4$, filtered and concentrated in vacuo to give a brown oil. Purification by silica chromatography eluting with 50% EtOAc:nHex+ 2% TEA gave the desired product as an orange oil (18 mg, 7%)

$^1$H NMR (250 MHz, C$_6$D$_6$) δ 4.52 (2H, app s), 4.19-4.15 (14H, m), 3.91 (4H, s), 3.54 (2H, t, J=7.3), 2.64 (2H, t, J=7.3), 1.69-1.43 (26H, m); m/z (ESI μTOF, M+H) calcd for C$_{36}$H$_{52}$NOS$_2$Fe$_2$ m/z 690.2143 found 690.2158. Electrochemical potential (DPV) 369 mV.

Example 9: 6-(bis((2-tert-butyl-sulfinylferrocenyl)1-methylferrocenyl)amino)hexan-1-ol 6-(bis((2-tert-butyl-sulfinylferrocenyl)1-methylferrocenyl)amino)hexan-1-ol was synthesised as shown in the scheme below.

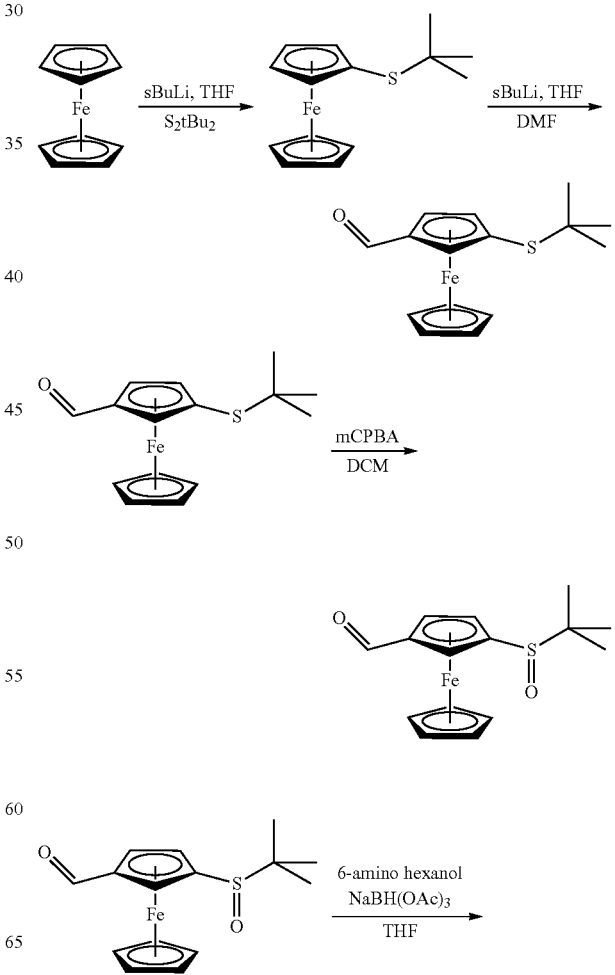

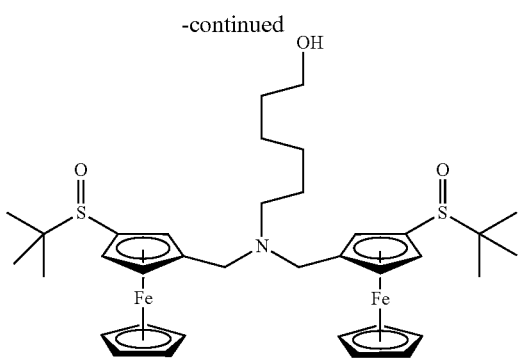

3-tert-Butylsulfinyl ferrocene carboxaldehyde (26.5 mg, 0.083 mmol) was dissolved in dry THF (1 cm$^3$), treated with 6-amino-hexan-1-ol (4.8 mg, 0.041 mmol). The brown solution was stirred for 10 mins before sodium trixacetoxyborohydride (34 mg, 0.2 mmol) was added in one portion. The brown suspension was then stirrer at room temperature overnight. After this time the material was concentrated in vacuo to give a brown solid. Purification by silica chromatography eluting with 2.5% MeOH:CH$_2$Cl$_2$+2% NH$_3$OH to give the desired product as a yellow oil (4 mg, 14%)

$^1$H NMR (250 MHz, C$_6$D$_6$) δ 5.12 (2H, app s), 4.92 (2H, app s), 4.39 (14H, m), 4.22 (4H, s), 3.69 (2H, t, J=7.1 Hz), 2.45 (2H, t, J=7.1 Hz), 1.50-1.18 (26H, m), m/z (ESI μTOF, M+H) calcd for C$_{36}$H$_{52}$NO$_3$S$_2$Fe$_2$ m/z 722.2087 found 722.2089, m/z; Electrochemical potential (DPV) 532 mV.

Example 10: General Synthetic Procedure for Attaching Phosphoramidite Functional Group

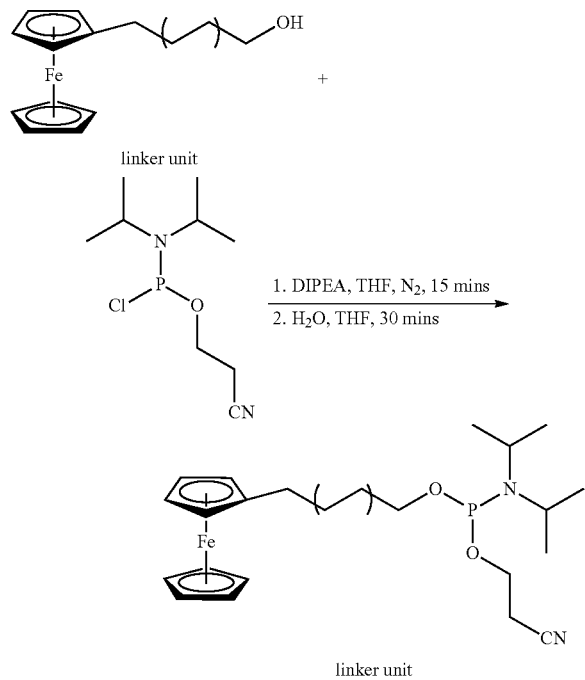

The ferrocenyl derivative shown as a starting material in the above reaction scheme is illustrative, and may be replaced by a molar equivalent of any of the compounds made in Examples 1 to 9 above.

N,N-diisopropylethylamine (0.4 mL, 8.4 mmol) was added to a stirred solution of the ferrocene derivative (2.1 mmol) in dry THF (25 mL) under a nitrogen atmosphere, 2-cyanoethyldiisopropylchlorophosphoramidite (0.2 ml, 3.15 mmol) was added dropwise and the resulting mixture was stirred for 15 mins. MilliQ filtered water (200 mL) was added and the solution was stirred for a further 30 mins. Ethyl Acetate-Triethylamine (1:1, 25 mL) was added, a precipitate formed. The mixture was washed with saturated NaCHCO$_3$ (25 mL) and MilliQ filtered water (25 mL). The organic fraction was dried over MgSO$_4$ and the solvent was removed under vacuo. The crude product was then purified by silica gel chromatography (petroleum ether:ethyl acetate 9:1).

Example 11—Binding of Labels to Protein

The labels of the invention are attached to a peptide by attachment of the label to a free amine of, for example, a lysine residue in the peptide. Attachment may be accomplished conventional techniques including functionalisation of the labelling compound to form an active NHS ester and reaction of the functionalised ester with the free amine group of the peptide.

Example 12—Binding of Labels to Microparticles

A biotin molecule is coupled to a label, for example a label as made in any of Examples 1 to 9. The biotinylation can be carried out in an automated oligonucleotide synthesiser or using standard laboratory conditions by reaction of ferrocenyl phosphoramidite label with N-hydroxysuccinimide (NHS) esters of biotin.

Paramagnetic treptavidin particles are washed ×3 (phosphate buffer) and mixed with biotinylated label, followed by incubation for 1 hour at room temperature with mixing. The particles are washed ×2 (phosphate buffer) and washed ×1 (PCR buffer). They are resuspended in final buffer (PCR buffer). Following each wash step the supernatants are tested for electrochemical signal, and if necessary washing is repeated until the supernatants show no indication of free electrochemical label.

These particles are assayed at a range of concentrations to validate that the observed electrochemical signal is attributable to the label coupled to the magnetic particles, using magnetic capture of the particles and resuspension in a range of buffer volumes.

In Table 5 below, the electrode potentials of the compounds made in Examples 1 to 5, 8 and 9 are listed, together with the comparison value for N,N-diferrocenylmethyl-6-aminohexanol, a compound in which the ferrocenyl groups are unsubstituted. A method for synthesis of N,N-diferrocenylmethyl-6-aminohexanol is disclosed in WO2012/085591.

TABLE 5

Effect on electrode potential of substituents on ferrocenyl moieties

| Example | Fc substituent | Electrode potential |
| --- | --- | --- |
| A | None | 275 mV |
| 1 | 1'-Iodo | 442 mV |
| 2 | 1'-(4-Nitrophenyl) | 437 mV |
| 3 | 1'-Furanyl | 339 mV |
| 4 | 2-di-t-butylphosphinyl | 512 mV |
| 5 | 1'-Chloro | 452 mV |

TABLE 5-continued

Effect on electrode potential of substituents on ferrocenyl moieties

| Example | Fc substituent | Electrode potential |
| --- | --- | --- |
| 8 | 2-tert-butyl-sulfidyl | 369 mV |
| 9 | 2-tert-butyl-sulfidyl | 532 mV |

The data in the above table shows that the compounds of Examples 1 to 5, 8 and 9 provide useful electrochemically active labels. The labels may be used to provide an electrochemical signal within a desired range of values. They may be useful as alternative labels to other labelling compounds with similar potential values, for example, where those other labelling compounds have disadvantageous properties in the assay in question, for example, incompatibility with impurities or other components present in the assay or incompatibility with the measurement conditions, any of which could affect measurement sensitivity. As well, or instead, they may be used with one or more other labels in a multiplex assay in which more than one label is present to provide two or more determinations in a single sample, the use of two or more labels with different electrochemical properties in those circumstances permitting effective distinction between measurements relating to the respective species to be determined.

What is claimed is:

1. A method of detecting a nucleic acid, the method comprising:
    contacting the nucleic acid with a complementary nucleic acid probe under conditions to allow hybridization between said probe and an amplicon; and
    selectively degrading the probe, wherein the probe is labelled with a compound selected from the group consisting of: 6-(bis((2-tert-butyl-sulfonylferrocenyl) 1methylferrocenyl) amino)hexan-1-ol, 6-(bis((2-di-tert-butyl-phosphinyl-ferrocenyl)1-methylferrocenyl) amino)hexan-1-ol, 6-(bis((2-tert-butyl-sulfinylferrocenyl)1methylferrocenyl) amino)hexan-1-ol, and 6-(bis((2-tert-butyl-sulfidylferrocenyl) 1methylferrocenyl) amino)hexan-1-ol.

2. The method of claim 1, further comprising measuring electrochemical activity of the compound labelling the probe, wherein said electrochemical activity is dependent either quantitatively or qualitatively on the degradation of the probe.

* * * * *